(12) United States Patent  
Katzman et al.

(10) Patent No.: US 9,186,155 B2  
(45) Date of Patent: Nov. 17, 2015

(54) SACROILIAC JOINT STABILIZATION METHOD

(71) Applicant: NuTech Spine, Inc., Birmingham, AL (US)

(72) Inventors: Scott Katzman, Palm Beach Gardens, FL (US); Joshua Appel, Parland, FL (US); Behnam Myers, Sunny Isles, FL (US); Jeffrey Oppenheimer, Boca Raton, FL (US); Robert Simon, West Palm Beach, FL (US); Travis Greenhalgh, Boca Raton, FL (US); Najeeb Reyes, Miami, FL (US); Gregory J. Yager, Mount Olive, AL (US); Howard P. Walthall, Jr., Birmingham, AL (US)

(73) Assignee: NuTech Spine, Inc., Birmingham, AL (US)

( * ) Notice: Subject to any disclaimer, the term of this patent is extended or adjusted under 35 U.S.C. 154(b) by 0 days.

(21) Appl. No.: 13/826,564

(22) Filed: Mar. 14, 2013

(65) Prior Publication Data

US 2014/0277165 A1 Sep. 18, 2014

(51) Int. Cl.

| A61B 17/88 | (2006.01) |
|---|---|
| A61B 17/16 | (2006.01) |
| A61B 17/17 | (2006.01) |
| A61B 17/70 | (2006.01) |
| A61B 17/02 | (2006.01) |

(52) U.S. Cl.  
CPC ......... *A61B 17/1615* (2013.01); *A61B 17/1671* (2013.01); *A61B 17/1757* (2013.01); *A61B 17/7055* (2013.01); *A61B 17/7076* (2013.01); *A61B 2017/0256* (2013.01)

(58) Field of Classification Search  
CPC .............. A61B 17/56; A61B 17/1697; A61B 17/7032; A61B 17/1615; A61B 17/1671; A61B 17/7076; A61B 17/7055; A61B 17/1757; A61B 17/70; A61B 2017/0256  
USPC ......................................................... 606/279  
See application file for complete search history.

(56) References Cited

U.S. PATENT DOCUMENTS

| 5,334,205 A * | 8/1994 | Cain ............................. 606/96 |
|---|---|---|
| 2008/0009861 A1 * | 1/2008 | Stark ............................. 606/61 |
| 2008/0097436 A1 * | 4/2008 | Culbert et al. .................. 606/61 |
| 2009/0149857 A1 * | 6/2009 | Culbert et al. .................. 606/80 |
| 2011/0087294 A1 * | 4/2011 | Reiley .......................... 606/279 |
| 2011/0087296 A1 * | 4/2011 | Reiley et al. .................. 606/303 |
| 2011/0166575 A1 * | 7/2011 | Assell et al. .................... 606/79 |
| 2011/0238181 A1 * | 9/2011 | Trieu ........................ 623/17.11 |
| 2012/0010620 A1 * | 1/2012 | Petersen ........................ 606/80 |
| 2012/0232658 A1 * | 9/2012 | Morgenstern Lopez et al. ......................... 623/17.16 |
| 2012/0310348 A1 * | 12/2012 | Pafford et al. ............. 623/17.16 |

* cited by examiner

*Primary Examiner* — Jerry Cumberledge  
*Assistant Examiner* — Tessa Matthews  
(74) *Attorney, Agent, or Firm* — C. Brandon Browning; Maynard Cooper Gale

(57) ABSTRACT

A method for treating back pain by stabilizing the sacroiliac joint. The method includes fusing a sacrum bone to an ilium bone or otherwise mechanically immobilizing the sacroiliac joint by inserting at least two implants into voids formed within or between the articular surfaces of each sacroiliac joint of a patient without substantially distracting the joint. The voids are arranged within each joint at either a converging orientation or a diverging orientation. A kit containing the implants and tools required to insert the implants into the joint are also described.

29 Claims, 23 Drawing Sheets

SACROILIAC JOINT STABILIZATION METHOD

FIELD OF THE INVENTION

The present invention is directed to a sacroiliac joint stabilization method for treating back pain, and more particularly, to a surgical procedure for fusing the sacroiliac joint, the procedure including inserting a pair of implants between the articular surfaces of the sacroiliac joint at converging or diverging orientations in a manner that does not substantially distract the joint.

BACKGROUND OF THE INVENTION

The sacroiliac joint is a diarthrodial joint that joins the sacrum to the ilium bones of the pelvis. In the sacroiliac joint, the sacral surface has hyaline cartilage that moves against fibrocartilage of the iliac surface. The spinal column is configured so that the weight of the upper body rests on the sacroiliac joints at the juncture of the sacrum and ilia. Stress placed on the sacroiliac joints in an upright position of the body makes the lower back susceptible to injury.

Disorders of the sacroiliac joint can cause low back and radiating buttock and leg pain in patients suffering from degeneration and/or laxity of the sacroiliac joint. In some cases, the sacroiliac joint can undergo degeneration of the cartilaginous surfaces of the joint, similar to other articulating joints, which causes significant pain. The sacroiliac joint is also susceptible to trauma, with resulting degeneration, fracture or instability. It is estimated that disorders of the sacroiliac joint are a source of pain for millions of people suffering from back and radicular symptoms.

Non-surgical treatments, such as medication, injection, mobilization, rehabilitation and exercise can be effective. However, they may fail to permanently relieve the symptoms associated with these disorders. Surgical treatment of these disorders includes stabilization and/or arthrodesis. Stabilization can include the use of bone screws that are directly threaded across the joint. Arthrodesis may include immobilization of a joint and the removal of all of part of the cartilage from within the joint, permitting bone growth across the joint and resulting in a permanent fusion. The present disclosure describes an improvement over these prior art technologies.

SUMMARY OF THE INVENTION

The present invention is directed to a method for treating back pain by stabilizing the sacroiliac joint. The sacroiliac joint is stabilized by fusing a sacrum bone to an ilium bone or otherwise mechanically immobilizing the sacroiliac joint. The method includes inserting at least two implants into voids formed within or between the articular surfaces of each sacroiliac joint of a patient without substantially distracting the joint. The voids are arranged within each joint at either a converging orientation or a diverging orientation. The converging or diverging orientation of the implants permits translation of the joint along the path of one of the implants, as would be possible with implants oriented in a parallel fashion. A kit containing the implants and tools required to insert the implants into the joint are also described.

According to one aspect of the invention there is provided a method of stabilizing a sacroiliac joint including forming a first void and a second void within the articular surfaces of the sacroiliac joint and placing a first implant within the first void and a second implant within the second void. Each void is formed by inserting a wire into the posterior aspect of the sacroiliac joint, inserting a number of dilation tubes over the wire thereby dilating tissue and creating a posterior access to the sacroiliac joint. A drill guide having a distal end with a pair of opposing teeth is slid over or through the dilation tube and the teeth inserted into a space between the ilium bone and the sacrum bone for stabilizing the drill guide. A drill bit is then inserted through the drill guide and into the sacroiliac joint and rotated for removing a portion of the cartilaginous articulating surfaces between the ilium bone and the sacrum bone.

After a void is formed, the drill bit and drill guide are removed from the dilation tube and an implant inserter device is provided. The inserter device includes a grasping member for holding an implant, a rotatable knob member and a screw member extending between the knob member and the grasping member. To insert the implant into the void, the insert and implant are passed through the dilation tube and the implant is placed at least partially within the void. The knob member is rotated to release the implant from the grasping member. A tamping device can be inserted through the dilation tube to fully seat or countersink the implant within void. A fusion promoting substance may also be passed through the dilation tube into the void.

According to another aspect of the invention there is provided a method of stabilizing a sacroiliac joint including forming a first void and a second void within the articular surfaces of the sacroiliac joint with the voids arranged in a converging orientation relative to one another. In particular, the first void is arranged to extend anterocranially within a caudal segment of the articular surfaces of the sacroiliac joint from a first opening formed in a crest of the first posterior margin section of the sacroiliac joint inferior to a level of a posterior superior iliac spine. The second void is arranged to extend anterocaudally within a midsection portion of the articular surfaces of the sacroiliac joint from a second opening formed in a second posterior margin section of the sacroiliac joint at or superior to the level of the posterior superior iliac spine.

Respective first and second implants are inserted into the first and second voids. The implants may be dense cancellous bone implants, the implants including a tapered distal end portion, a substantially flat proximal end face having a central protuberance extending axially therefrom and a midsection extending between the distal end portion and the proximal end face. The midsection includes a plurality of ridges configured for preventing the bone implant from backing out of the sacroiliac joint. The use of dense cancellous bone as an implant material permits and encourages bony in-growth throughout the body of the implant. When the implants are seated within the voids, it is preferred that the first implant has a longitudinal axis that crosses a longitudinal axis of the second implant at an angle ranging between 35 degrees and 55 degrees, 40 degrees and 50 degrees or 42 degrees and 47 degrees. The method of stabilizing the sacroiliac joint is performed with essentially no distraction of the sacroiliac joint by utilizing instruments provided in a kit containing the guide wire, one or more dilation tubes, a drill guide, a bone implant inserter and a drill bit having a cutting diameter that is substantially the same as the diameters of the bone implants. Preferably, the cutting diameter is about 0.5 mm less than the diameter of each bone implant.

According to another aspect of the invention there is provided a method of stabilizing a sacroiliac joint including forming a first void and a second void within the articular surfaces of the sacroiliac joint with the voids arranged in a diverging orientation relative to one another. In particular, the first void is arranged to extend anterocaudally within a caudal segment of the articular surfaces of the sacroiliac joint from a first opening formed in a first posterior margin section of the sacroiliac joint at or inferior to a level of a posterior superior iliac spine. The first opening is formed through a superior surface of the caudal segment of the articular surfaces of the sacroiliac joint. The second void extends anterocranially within a cranial segment of the articular surfaces of the sacroiliac joint from a second opening formed in a second posterior margin section of the sacroiliac joint at or superior to the level of the posterior superior iliac spine. The second opening is formed through a posterior surface of the cranial segment of the articular surfaces of the sacroiliac joint. Respective first and second implants are inserted into the first and second voids with essentially no distraction of the sacroiliac joint.

According to yet another aspect of the invention there is provided a method of stabilizing a sacroiliac joint including forming a first passageway extending anterocranially within the articular surfaces of the sacroiliac joint from a first opening formed in a first posterior margin section of the sacroiliac joint, forming a second passageway extending anterocaudually within the articular surfaces of the sacroiliac joint from a second opening formed in a second posterior margin section of the sacroiliac joint, and placing a first implant within the first void and a second implant within the second void.

A further understanding of the nature and advantages of the present invention will be realized by reference to the remaining portions of the specification and the drawings.

DETAILED DESCRIPTION OF THE INVENTION

The present invention is generally directed to a surgical procedure for stabilizing or immobilizing the sacroiliac joint. The procedure includes positioning a pair of implants within the articular surfaces of the sacroiliac joint in either a converging orientation or a diverging orientation. The procedure is carried out in a manner that minimizes distraction of the sacroiliac joint during insertion of the implants so that essentially no distraction of the joint occurs. By "essentially no distraction" it is meant less than 1 mm of distraction, preferably less than 0.6 mm of distraction, and more preferably less than about 0.5 mm of distraction, occurs between the articular surfaces of the sacroiliac joint of a patient.

Figure 1:
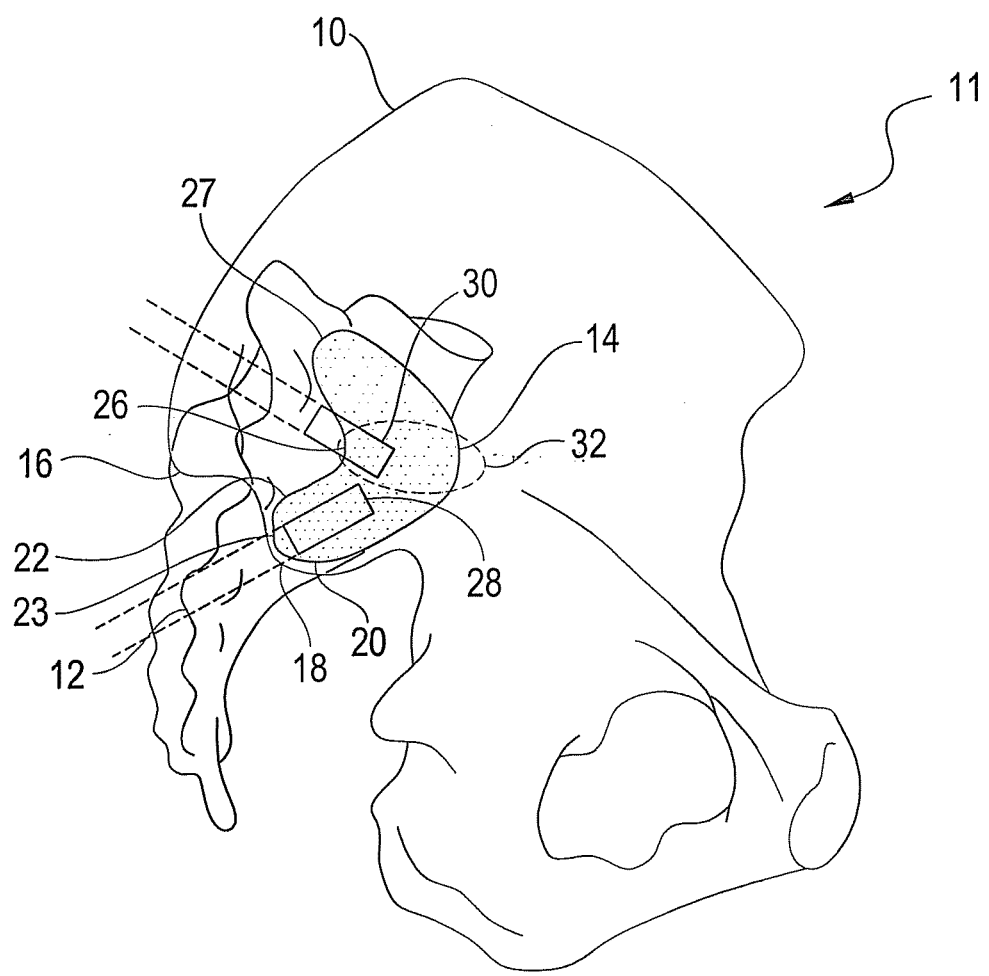
FIG. 1 is a lateral view of a pelvic region showing a first implant and a second implant operatively positioned between the articular surfaces of a sacroiliac joint in accordance with a first embodiment of the present invention.
Figure 2:
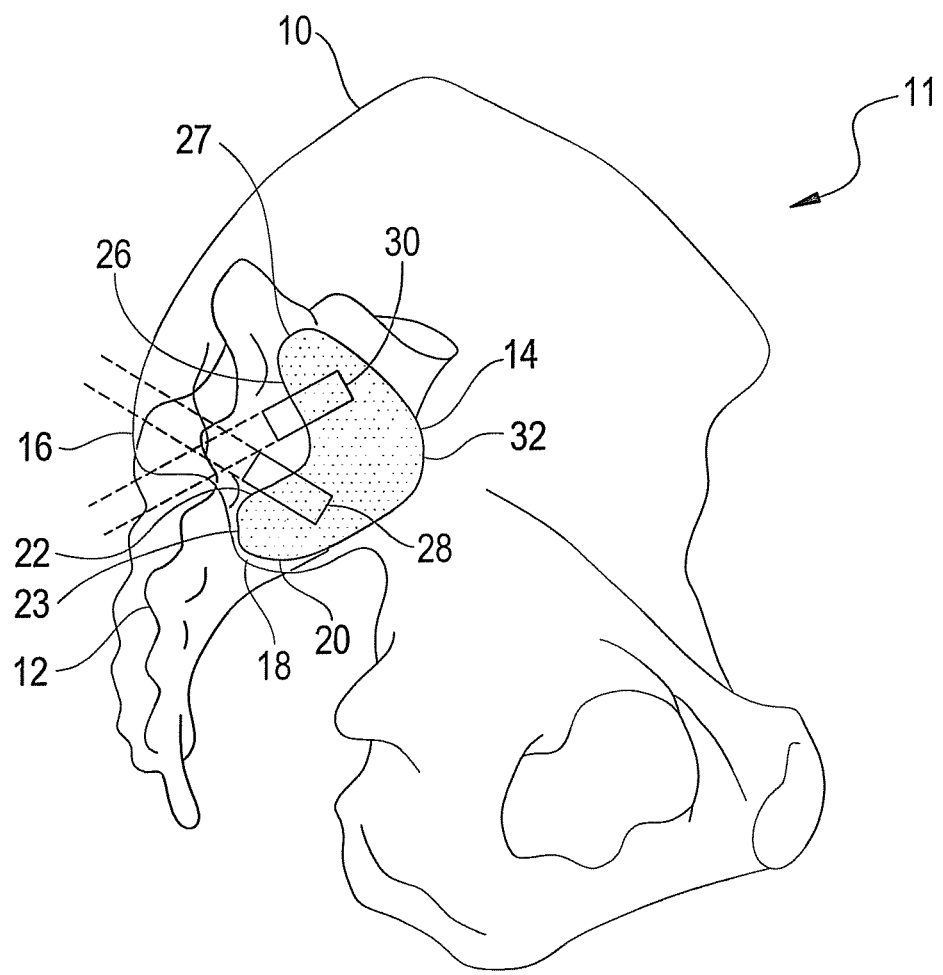
FIG. 2 is a lateral view of a pelvic region showing a first implant and a second implant operatively positioned between the articular surfaces of a sacroiliac joint in accordance with a second embodiment of the present invention.

FIG. 1 depicts a pair of implants arranged in the converging orientation 11 within the articular surfaces of a sacroiliac joint. FIG. 2 depicts a pair of implants arranged in the diverging orientation 13 within the articular surfaces of a sacroiliac joint. FIGS. 3 through 15 illustrate a surgical kit 15 and the various instruments of the kit used to carry out the sacroiliac implant procedure. FIGS. 16 through 31 illustrate the surgical steps of the procedure and, in particular, the manner in which the implants are introduce into the joint so to minimize distraction of the sacroiliac joint.

Referring to FIGS. 1 and 2, there is depicted a sacroiliac joint including an ilium 10, a sacrum 12 and articular surfaces 14 of ilium 10 and sacrum 12. Ilium 10 includes a posterior superior iliac spine 16 and a posterior inferior iliac spine 18. Articular surfaces 14 are generally L-shaped and include a caudal segment 20 having a first posterior or superior margin 22 with a first posterior crest 23 and a cranial segment 24 having a second posterior margin 26 with a second posterior crest 27.

As illustrated in FIG. 1, when arranged in converging orientation 11, a first or inferior implant 28 is positioned within a first void which extends from a first opening formed through posterior crest 23 of articular surfaces 14 of caudal segment 20 at a level inferior to posterior superior spine 16. First implant 28 is countersunk into the first void and extends anterocranially within caudal segment 20. A second or superior implant 30 is positioned within a second void which extends from a second opening formed in second posterior margin 26 of articular surfaces 14 at or superior to the level of posterior superior iliac spine 16. Second implant 30 extends anterocaudally within a midsection portion 32 of articular surfaces 14 that is formed between caudal segment 20 and cranial segment 24. Preferably, second implant 30 is embedded within articular surfaces 14 such that a posterior portion of the second implant is countersunk from at least about 1 mm to about 100 mm between the articular surfaces.

As illustrated in FIG. 2, when arranged in diverging orientation 13, first or inferior implant 28 is positioned within a first void which extends from a first opening formed in first posterior margin 22 of articular surfaces 14 at or inferior to a level of posterior superior iliac spine 16. First implant 28 extends anterocaudally within caudal segment 20 and is embedded within articular surfaces 14 such that a posterior portion of the first implant is countersunk from at least about 1 mm to about 100 mm between the articular surfaces. Second implant 30 is positioned within a second void which extends from a second opening formed in second posterior margin 26 of articular surfaces 14 at or superior to the level of posterior superior spine 16. Second implant 30 extends anterocranially within cranial segment 24 and, like first implant 28, is only partially embedded within articular surfaces 14.

Figure 3:
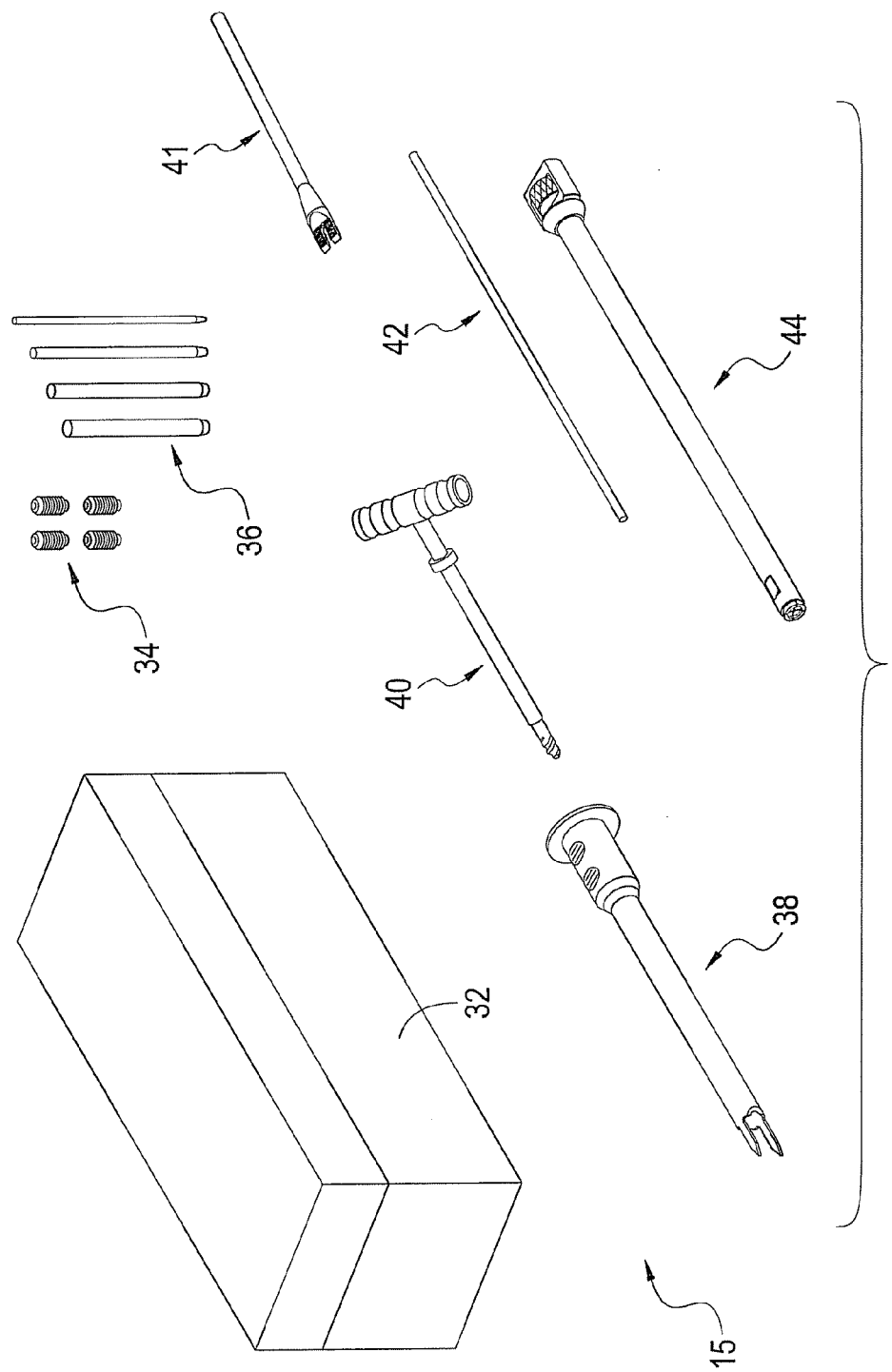
FIG. 3 is a schematic view of a kit containing instruments and implants for stabilizing a sacroiliac joint.

Referring to FIG. 3, there is illustrated surgical kit 15 and the various instruments of the kit used to carry out the sacroiliac joint fusion procedure of the present invention. Kit 15 includes an enclosure 32 having a base and a removable lid. Contained within enclosure 32 are a set of at least four dilation tubes 36, a drill guide 38, a drill 40, a k-wire 42, an implant inserter 44, and optionally, a joint locator 41. Kit 15 may also include a bone fusion promoting substance such as bone morphogenetic protein-2 (BMP-2) or stem cell-containing material. Kit 15 may further include at least four sacroiliac joint implants or dowels 34 (including a pair of implants 28 for inferior insertion and a pair of implants 30 for superior insertion); however, in most instances, dowels 34 are stored and transported separately from kit 15.

Figure 4:
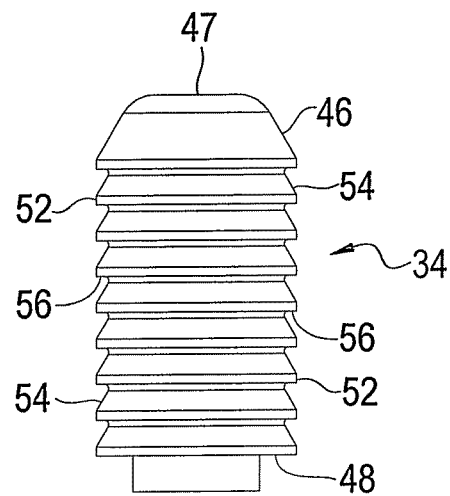
FIG. 4 is an elevational view of an implant of the kit of FIG. 3.
Figure 5:
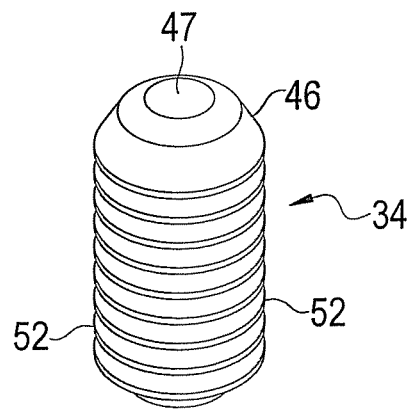
FIG. 5 is a perspective view of the implant of FIG. 4.

Referring to FIGS. 4 and 5, each implant 34 has a generally bullet-shaped appearance with a tapered first end 46 ending in a flat portion 47 and a substantially flat second end 48 having a cylinder-shaped protuberance 50 extending axially therefrom. Implant 34 further includes a midsection having a plurality of ridges 52 extending radially out therefrom. Each ridge 52 includes a first end side 54 which slopes inwardly and toward first end 46 and a second end side 56 which is arranged normal to the axis of the implant. Plurality of ridges 52 are provided to inhibit or prevent the implants from backing out of the articular surfaces of the sacroiliac joint once inserted there between.

Figure 6:
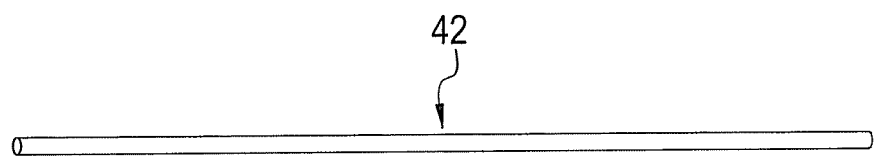
FIG. 6 is an elevational view of a guide wire of the kit of FIG. 3.

Referring to FIG. 6, k-wire 42 is a sterilized, sharpened, smooth stainless steel pin. K-wires are typically used in orthopedics to hold bone fragments together or to provide an anchor for skeletal traction. K-wires are often driven into the bone through the skin using a power or hand drill. In the present invention, k-wire 42 is used in combination with a direct A-P fluoroscopic view to locate pathways through the articular surfaces of the sacroiliac joint where implants 34 are to be inserted by acting as a guide for insertion of dilation tubes 36, joint locator 41 and drill guide 38.

Figure 7:
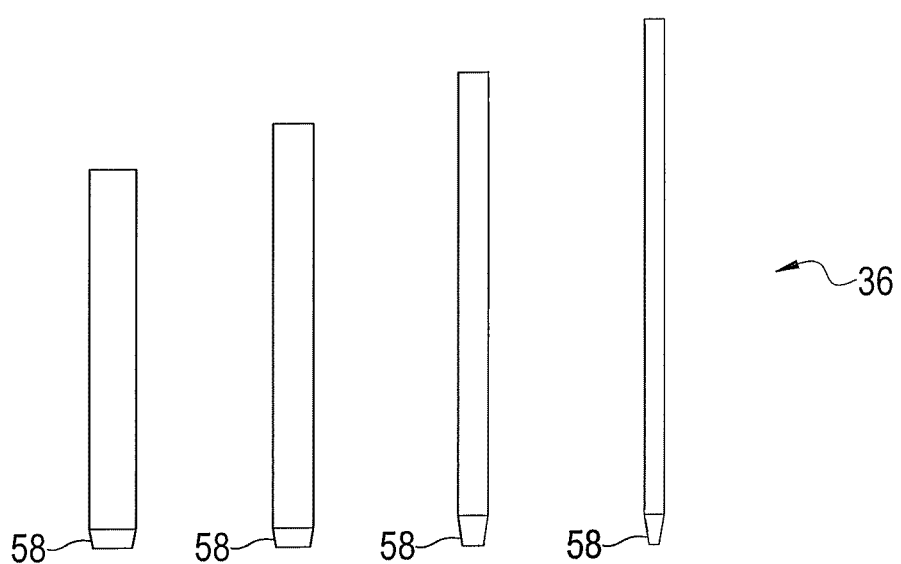
FIG. 7 is an elevational view of a plurality of dilation tubes of the kit of FIG. 3.

Referring to FIG. 7, dilation tubes 36 are represented by four hollow, metal tubes each having a tapered end 58, an inner diameter and an outer diameter. The inner and outer diameters of the respective tubes 36 differ, becoming progressively larger, which allows the tubes to be snuggly arranged coaxially within one another. Dilation tubes 36 are used to progressively enlarge a pathway through the skin and tissue to the articular surfaces of the sacroiliac joint as defined by k-wire 42 by placing the tubes one at a time, starting with the smallest tube, over k-wire 42.

Figure 8:
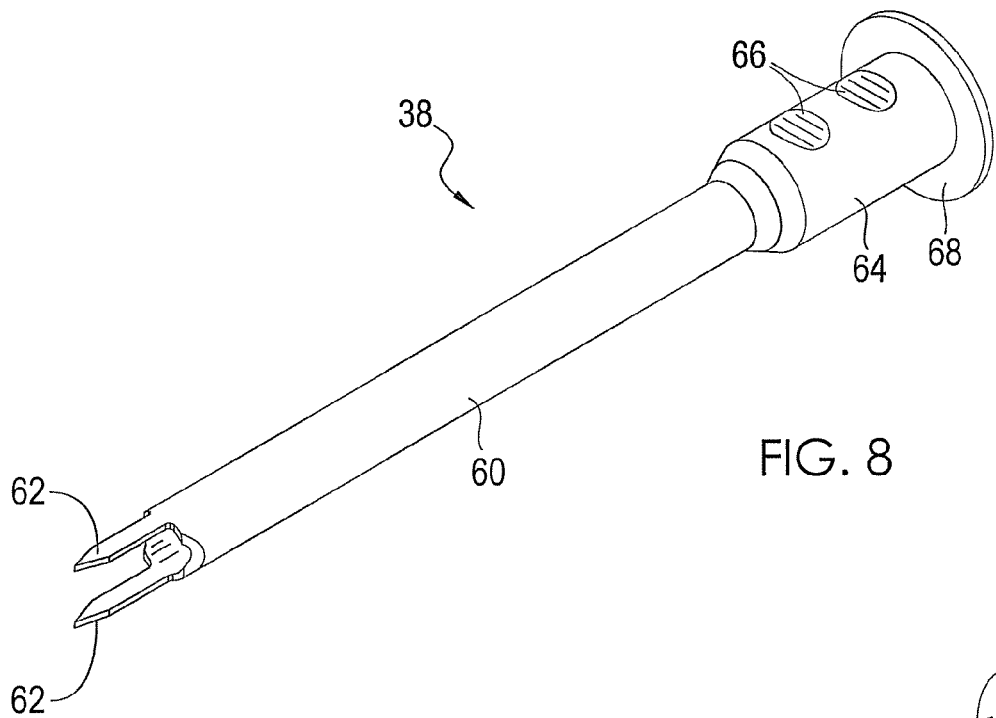
FIG. 8 is a distal end, perspective view of a drill guide of the kit of FIG. 3.
Figure 9:
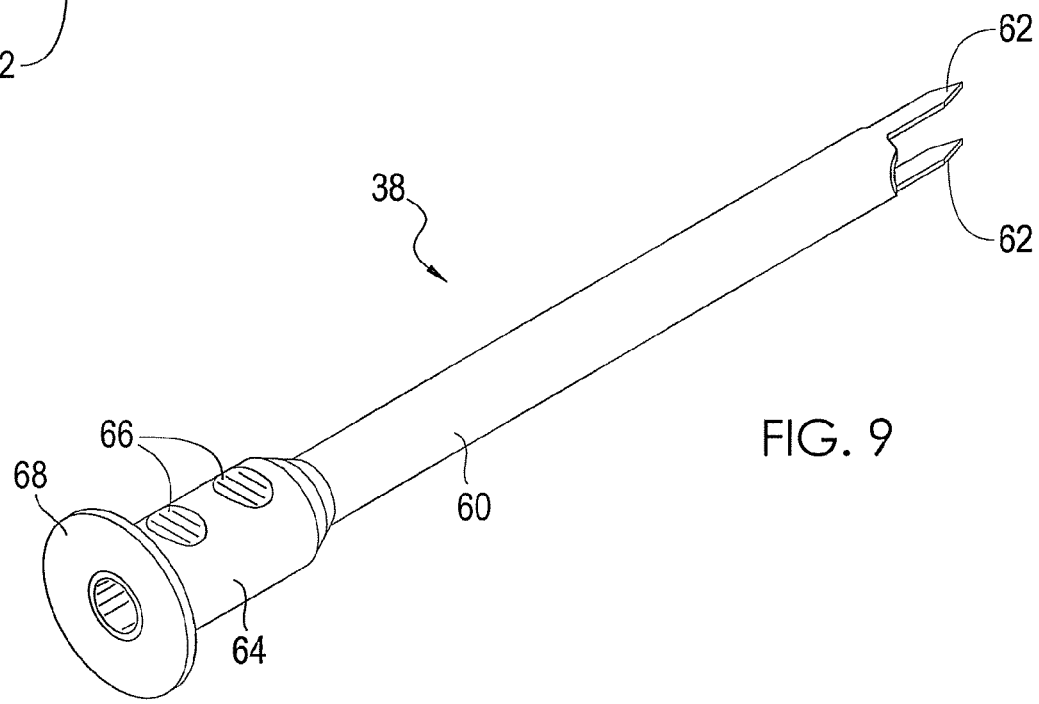
FIG. 9 is a proximal end, perspective view of the drill guide according to claim FIG. 8.

Referring to FIGS. 8 and 9, drill guide 38 includes a hollow middle section 60 having a distal end terminating in a pair of opposed acutely, pointed teeth 62. Teeth 62 are configured to locate and maintain the distal end of drill guide 38 within the sacroiliac joint directly posterior to the articular surfaces of the joint where holes are to be drilled therein. To assist with the handling of the instrument, drill guide 38 includes a handle portion 64 having an enlarged diameter relative the outer diameter of middle section 60. Handle portion 64 includes indentations 66 for receiving a physician's fingers and a flange portion 68.

Figure 10:
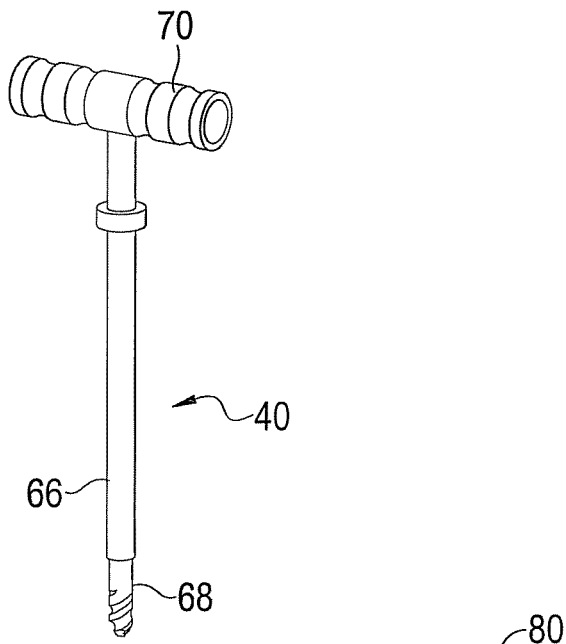
FIG. 10 is a perspective view of a drill bit of FIG. 3.
Figure 11:
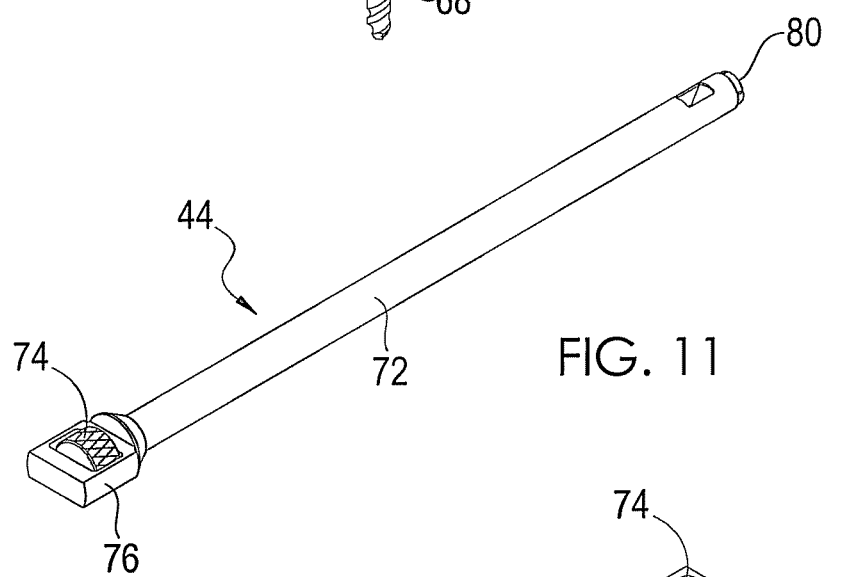
FIG. 11 is a proximal end, perspective view of an implant inserting device of the kit of FIG. 4.
Figure 12:
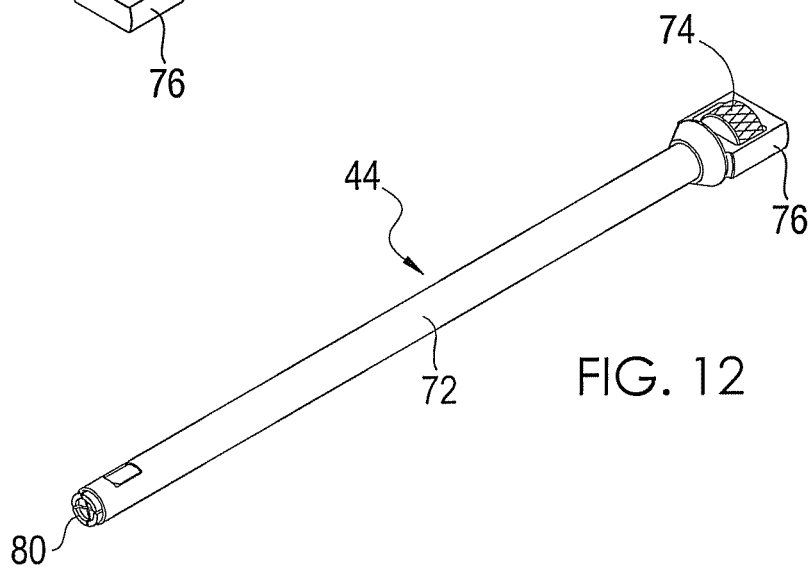
FIG. 12 is a distal end, perspective view of the implant inserting device of FIG. 11.
Figure 13:
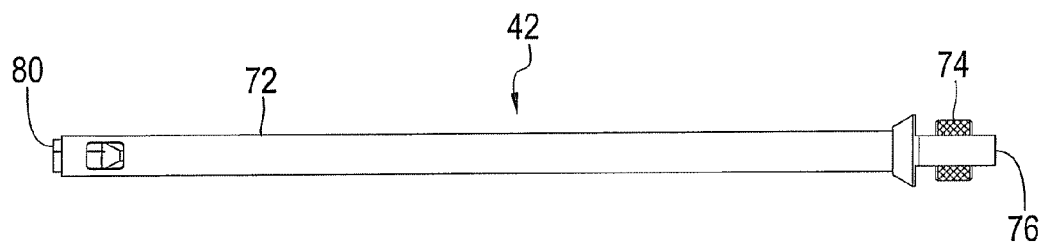
FIG. 13 is an elevational view of the implant inserting device of FIG. 11 showing the implant grasper, retracted in a grasping arrangement.
Figure 14:
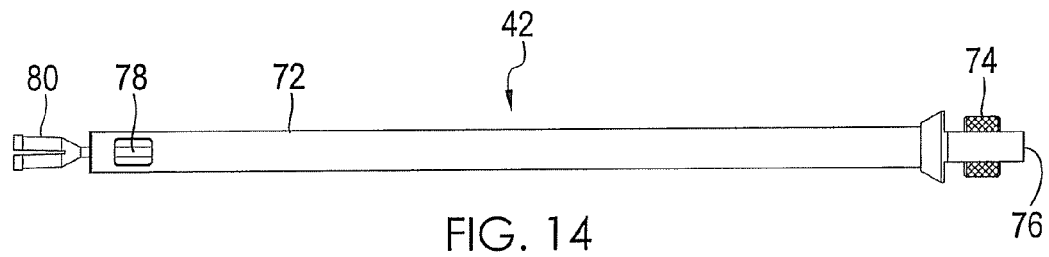
FIG. 14 is an elevational view of the implant inserting device of FIG. 11 showing the implant grasper, extended in a releasing arrangement.
Figure 15:
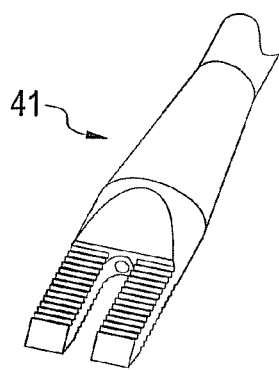
FIG. 15 is a perspective view of a joint locator device of FIG. 3.

Referring to FIG. 10 manual drill 40 includes a shaft 66 having a distal end terminating in a drill bit 68 and a proximal end terminating in a handle 70. Drill bit 68 has an outer diameter that, at its greatest diameter, is slightly less than the diameter of implants 36. This ensures that when placed in the holes formed within the articular surfaces by drill bit 68, the implants fit snuggly within the holes.

Referring to FIGS. 11 through 14, inserter 44 is composed a hollow tube 72 having a rotatable shaft extending there through. The proximal end of the shaft is coupled to a knob 74 contained within a knob housing 76. At the distal end of the rotatable shaft is a screw driven shaft 78 that is extendable from and retrievable into the distal end of hollow tube 72 upon the rotation of knob 74 and the rotatable shaft. An implant holder 80 having biased arms is coupled to the distal end of screw driven shaft 78. The biased arms are arranged to spread apart when maintained outside of the confines of the distal end of hollow tube 72. However, when retrieved into the distal end of hollow tube 72, a tapered portion 73 of the biased arms is arranged to interact with the inner wall of the hollow tube 72 to cause the biased arm to contract. In this manner, implant holder 80 is caused to selectively hold and release implant 34.

Figure 16:
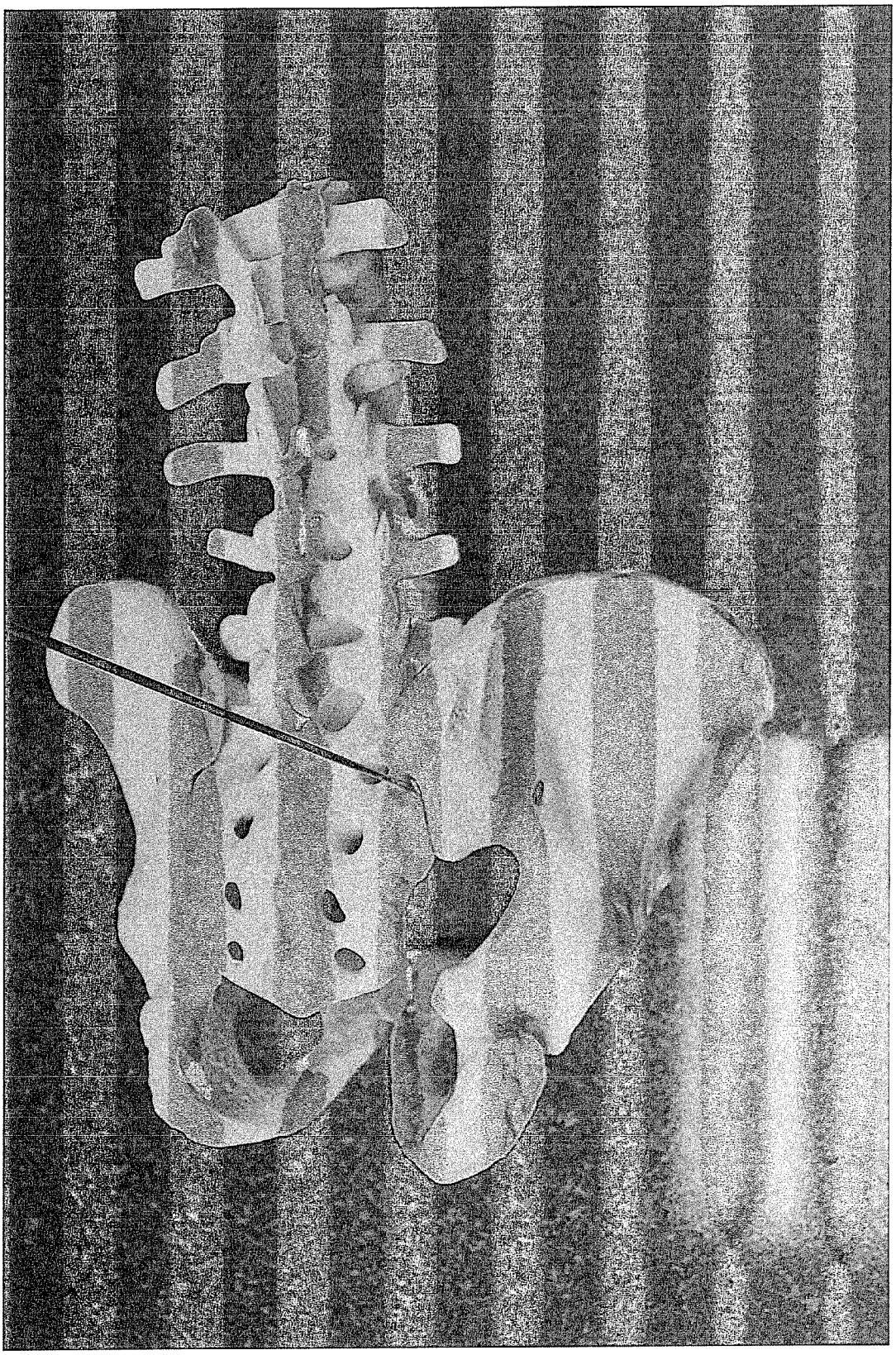
FIG. 16 is a perspective view of placement of a k-wire into a sacroiliac joint.
Figure 17:
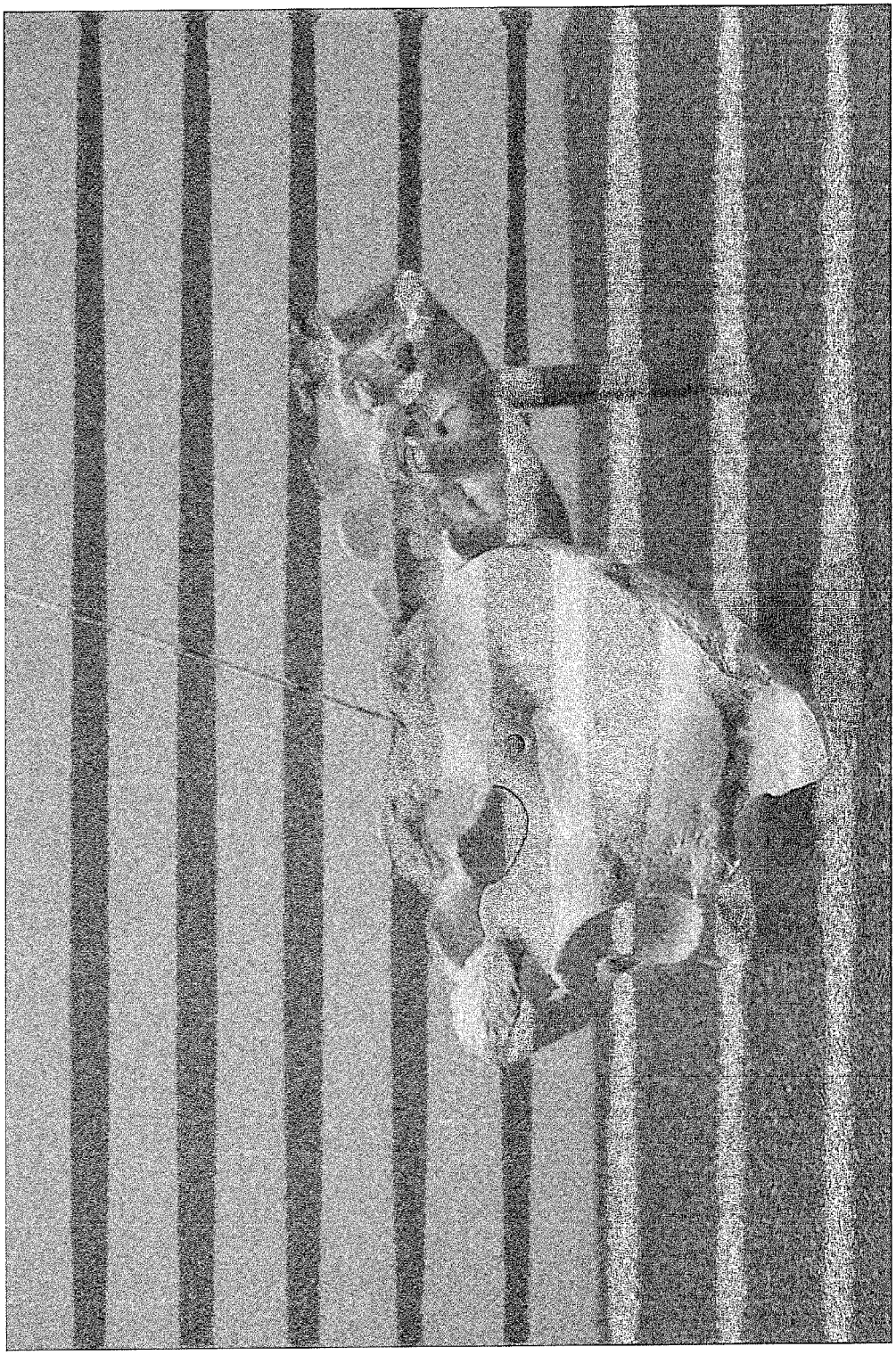
FIG. 17 is an elevational view of the k-wire and sacroiliac joint of FIG. 16.
Figure 18:
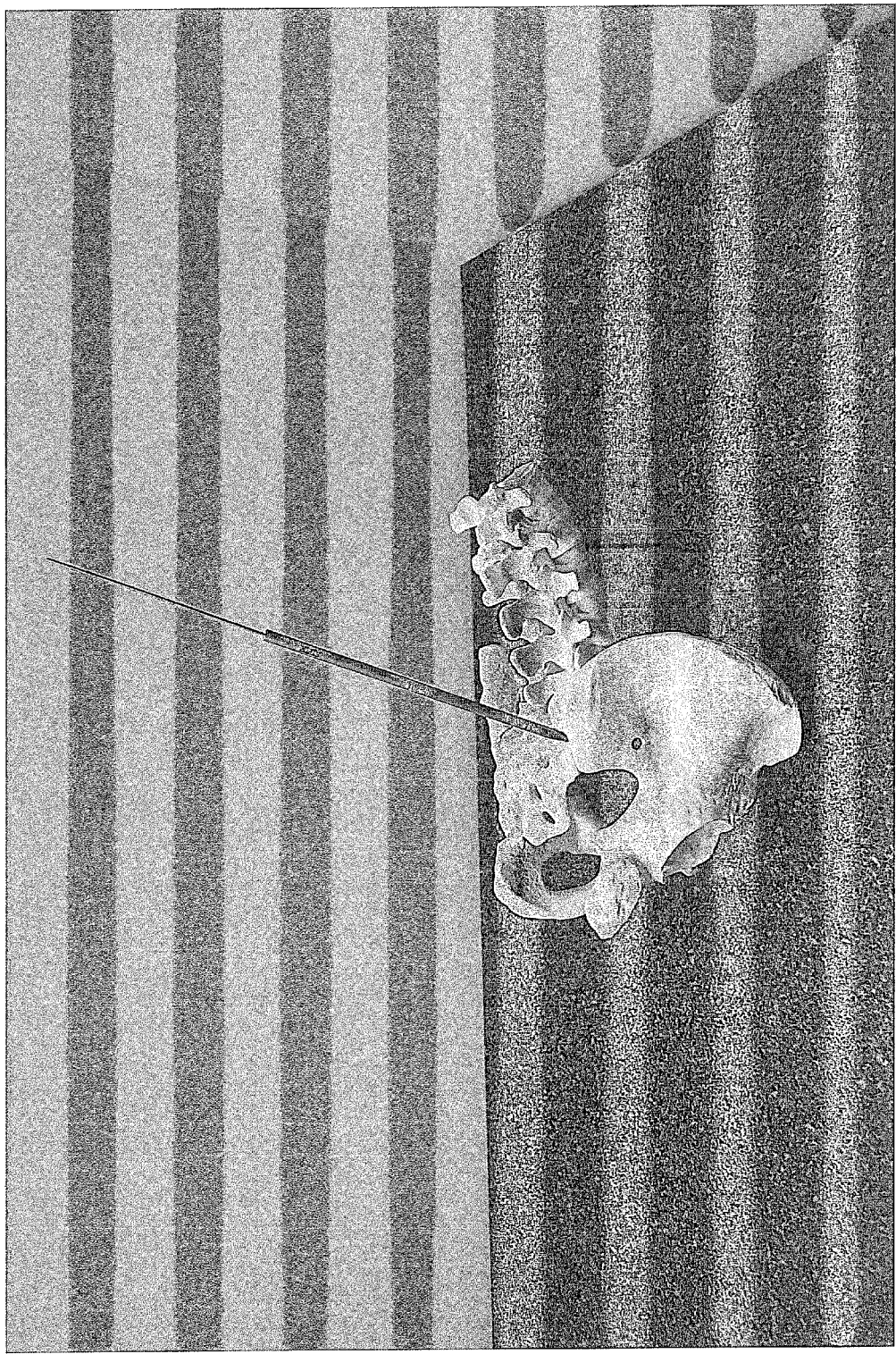
FIG. 18 is a perspective view of a first dilator inserted over the k-wire of FIG. 16.
Figure 19:
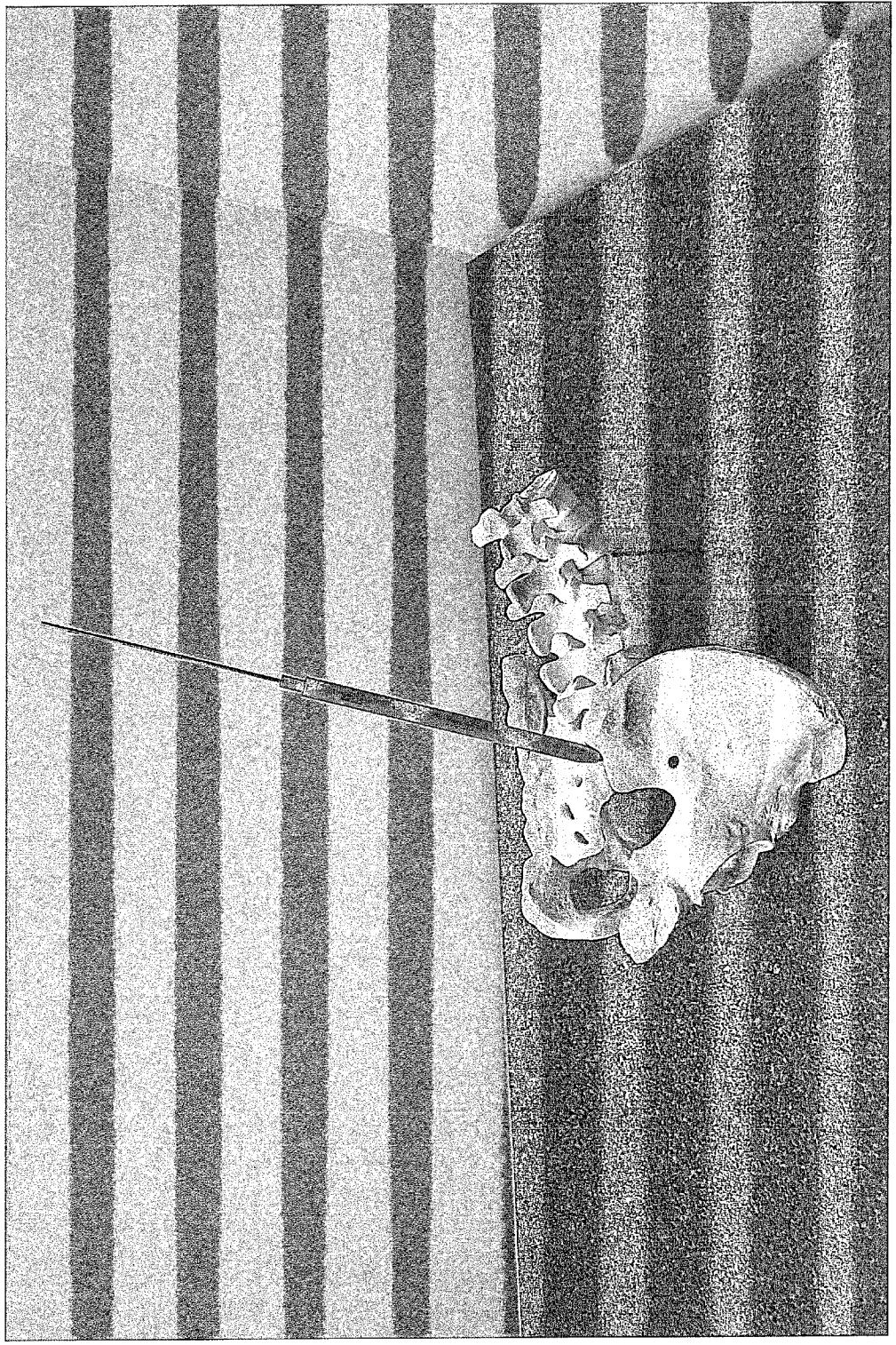
FIG. 19 is a perspective view of a second dilator inserted over the first dilator of FIG. 18.
Figure 20:
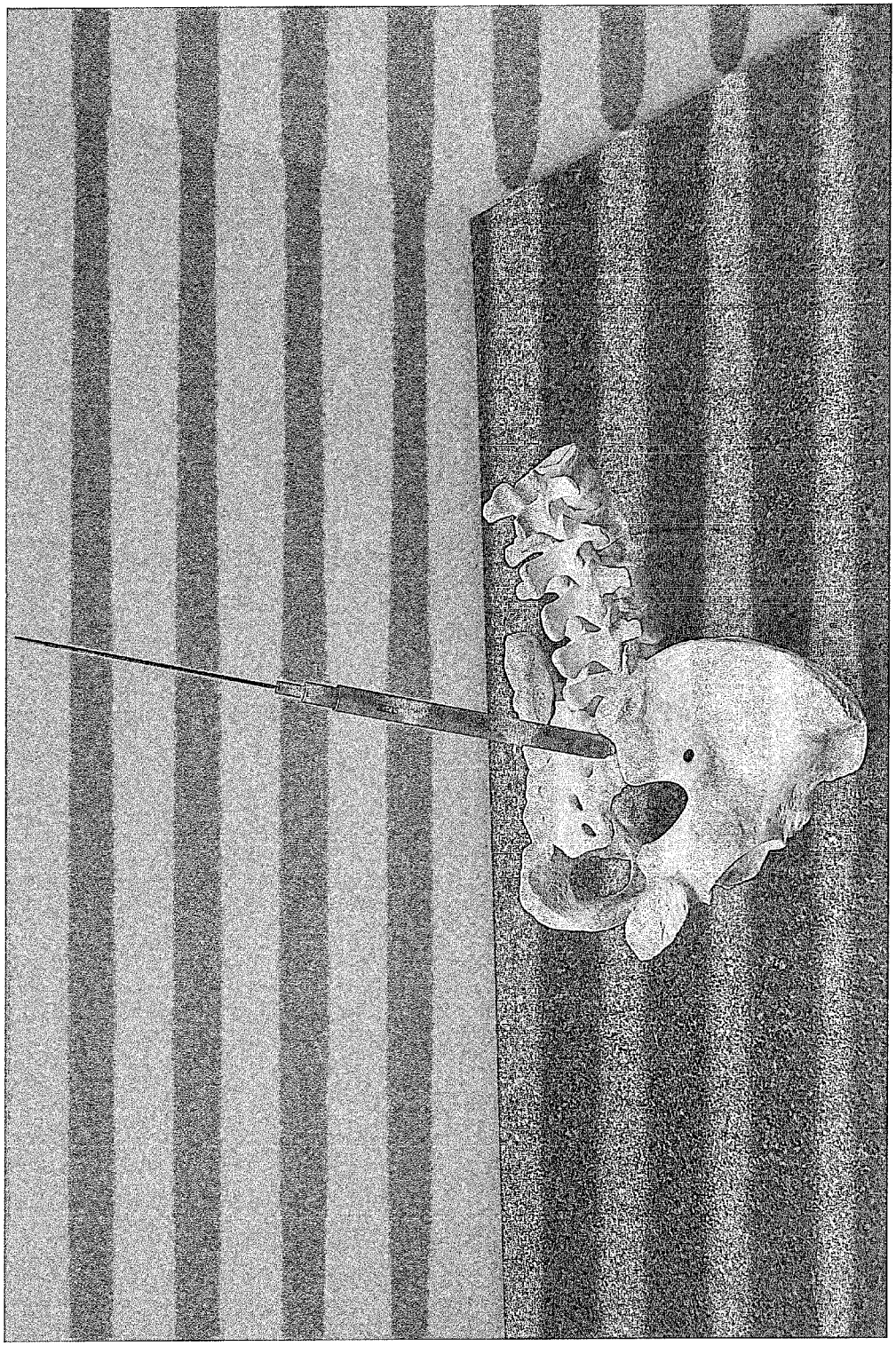
FIG. 20 is a perspective view of a third dilator inserted over the second dilator of FIG. 19.
Figure 21:
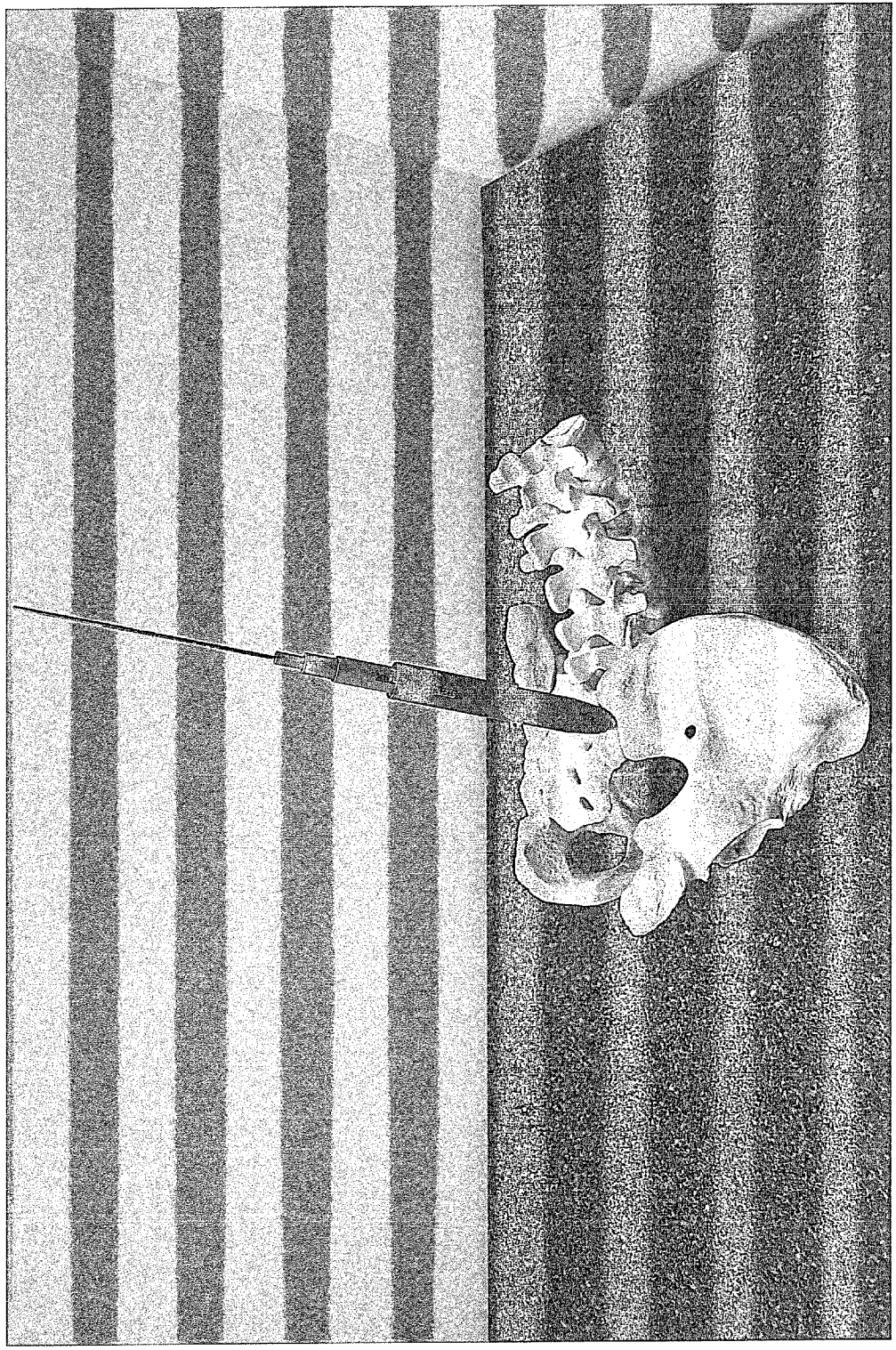
FIG. 21 is a perspective view of a fourth dilator inserted over the third dilator of FIG. 20.
Figure 22:
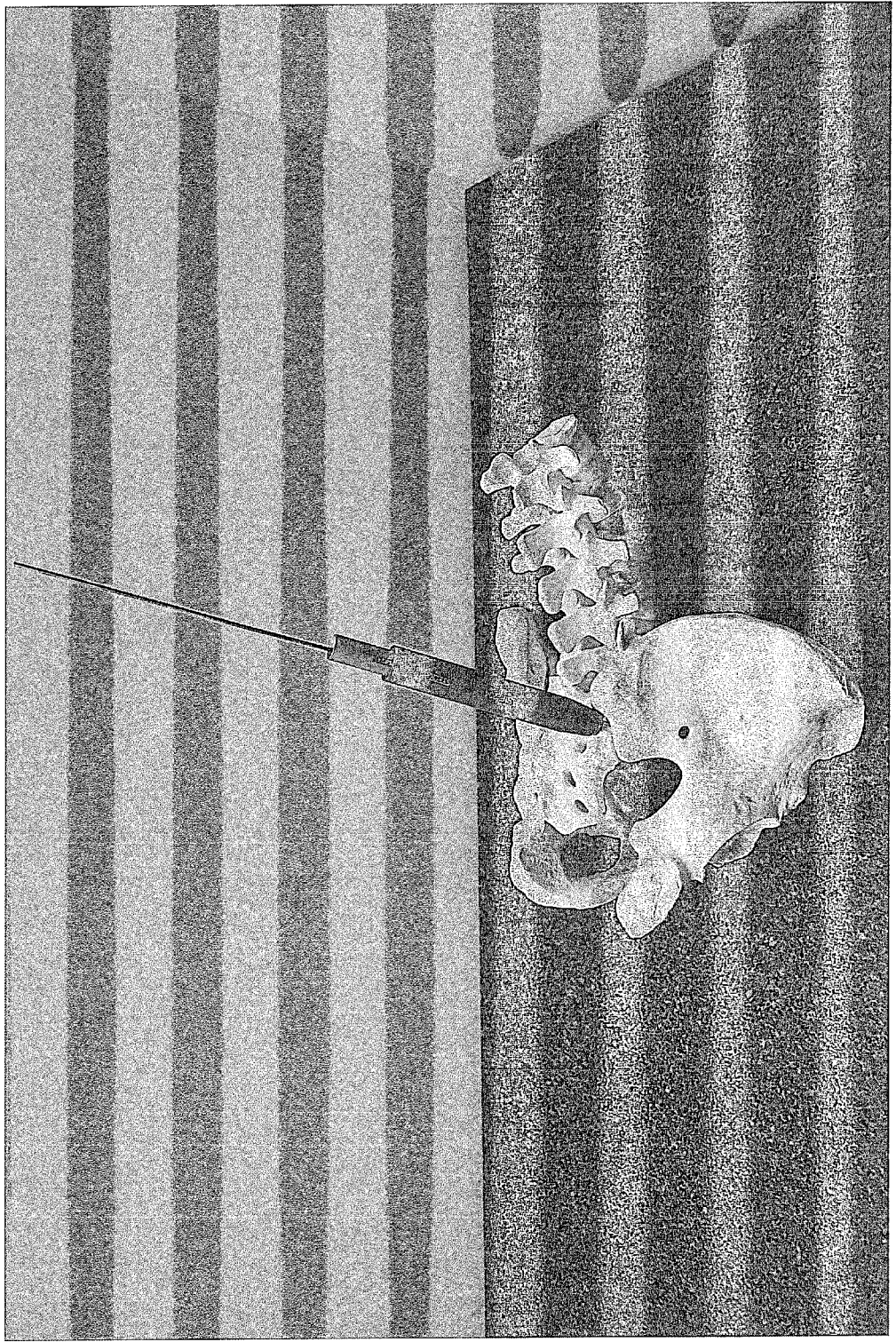
FIG. 22 is a perspective view of the fourth and third dilators of FIG. 21 with the first and second dilators removed.
Figure 23:
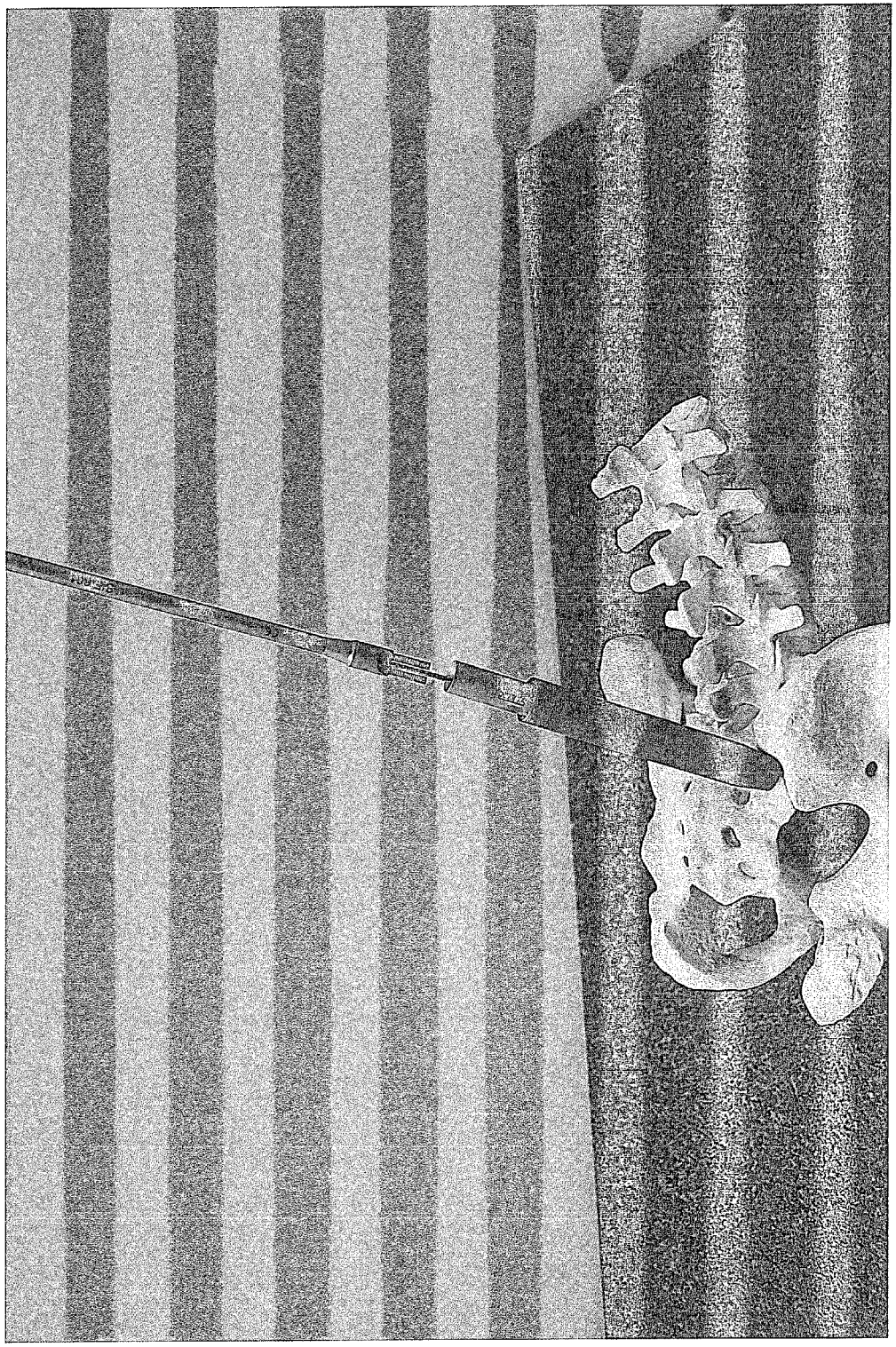
FIG. 23 is a perspective view of a joint locator partially inserted over the k-wire of FIG. 22.
Figure 24:
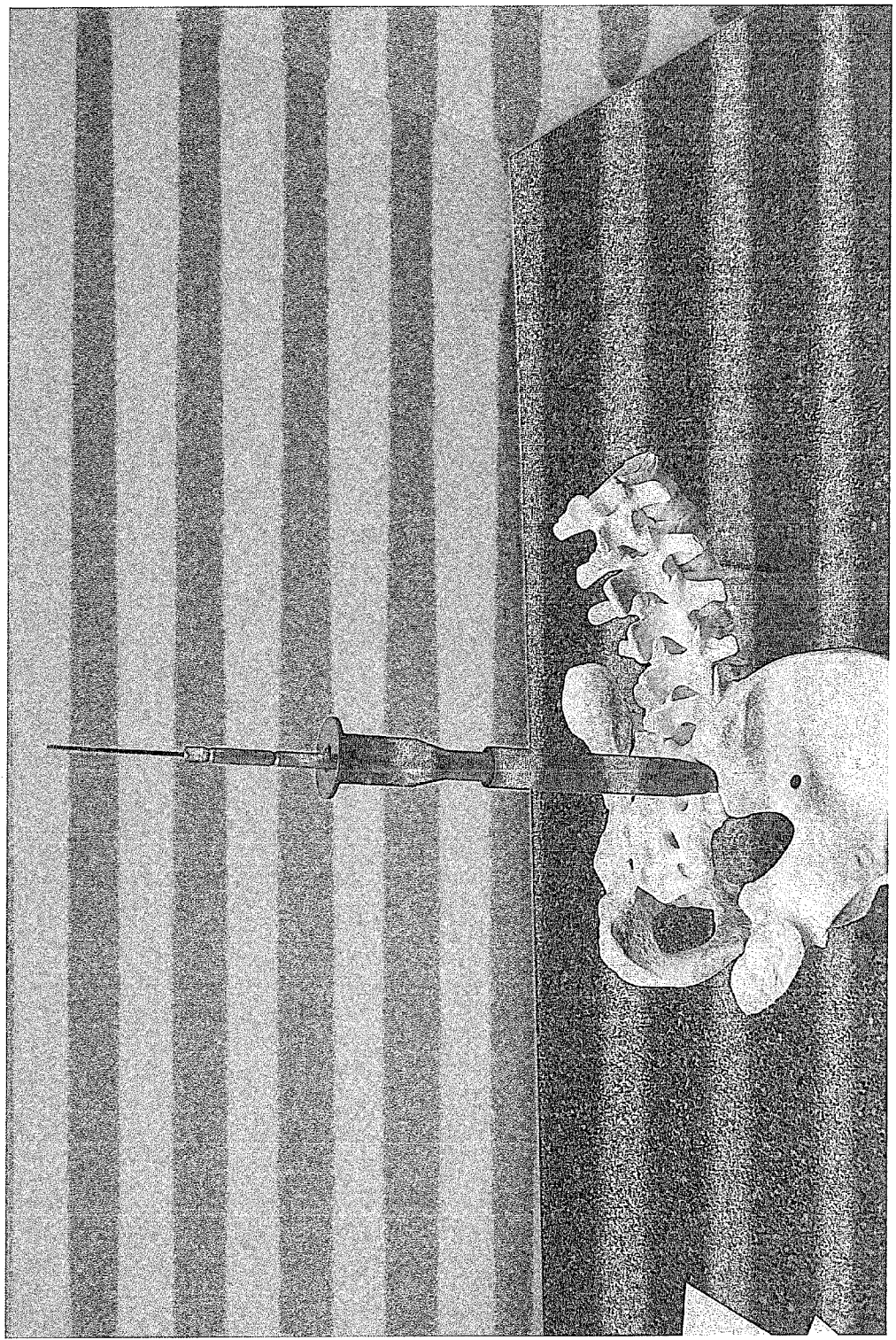
FIG. 24 is a perspective view of the joint locator of FIG. 23 inserted over the k-ware with a drill guide inserted between the joint locator and the fourth dilator.
Figure 25:
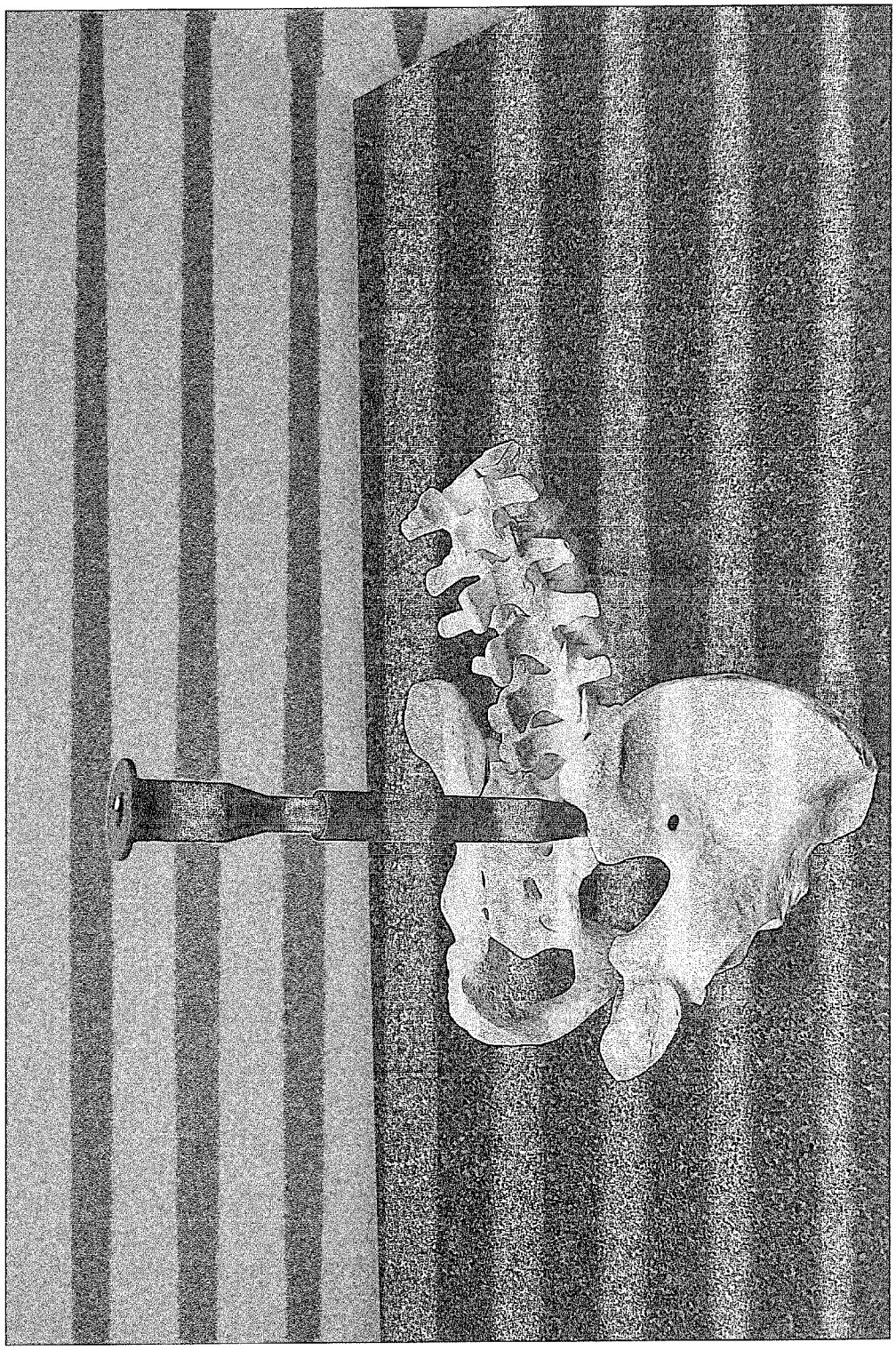
FIG. 25 is a perspective view of a drill guide inserted into the fourth dilator of FIG. 22 with the k-wire and the third dilator removed.
Figure 26:
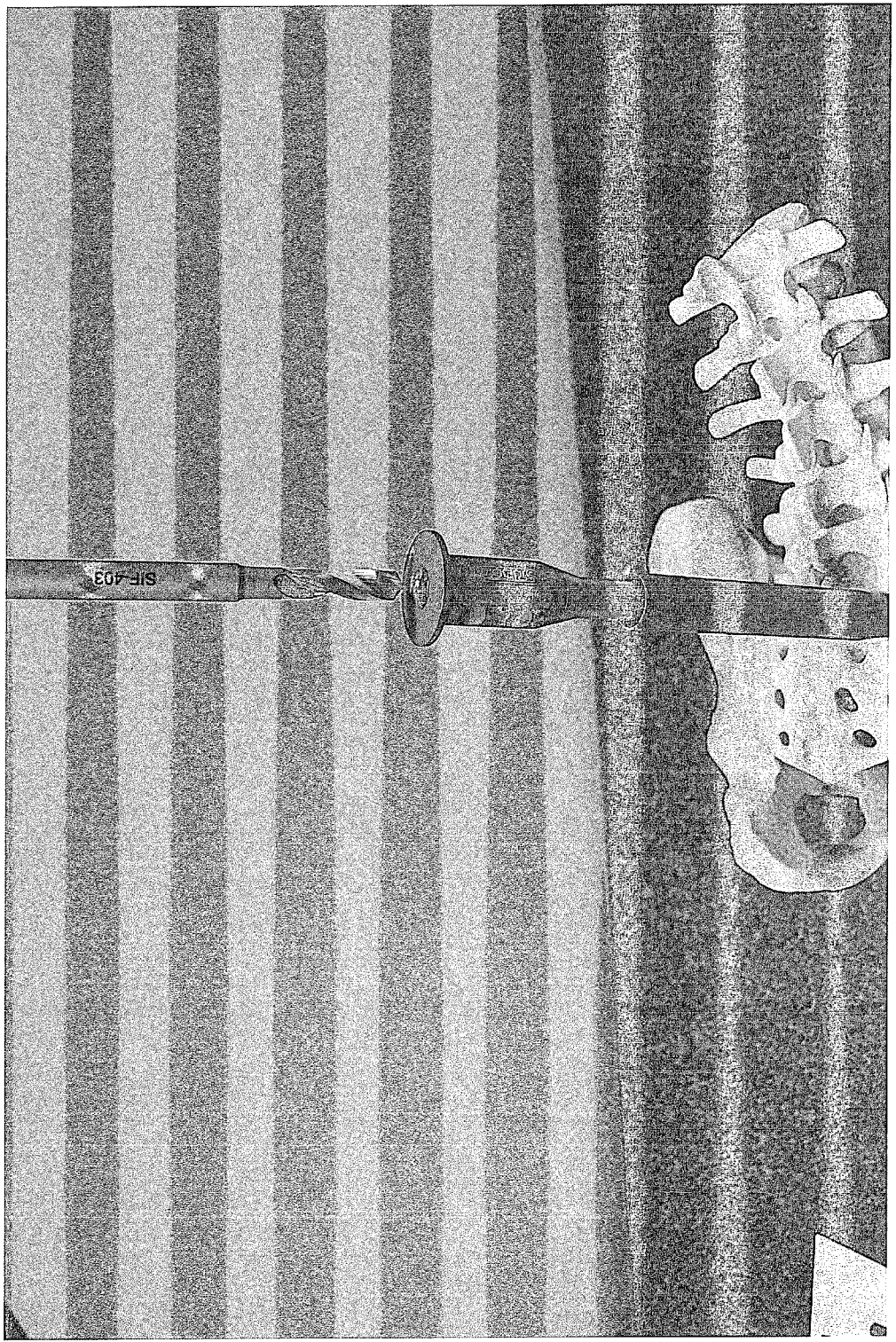
FIG. 26 is a perspective view of a drill bit being inserted into the drill guide of FIG. 25.
Figure 27:
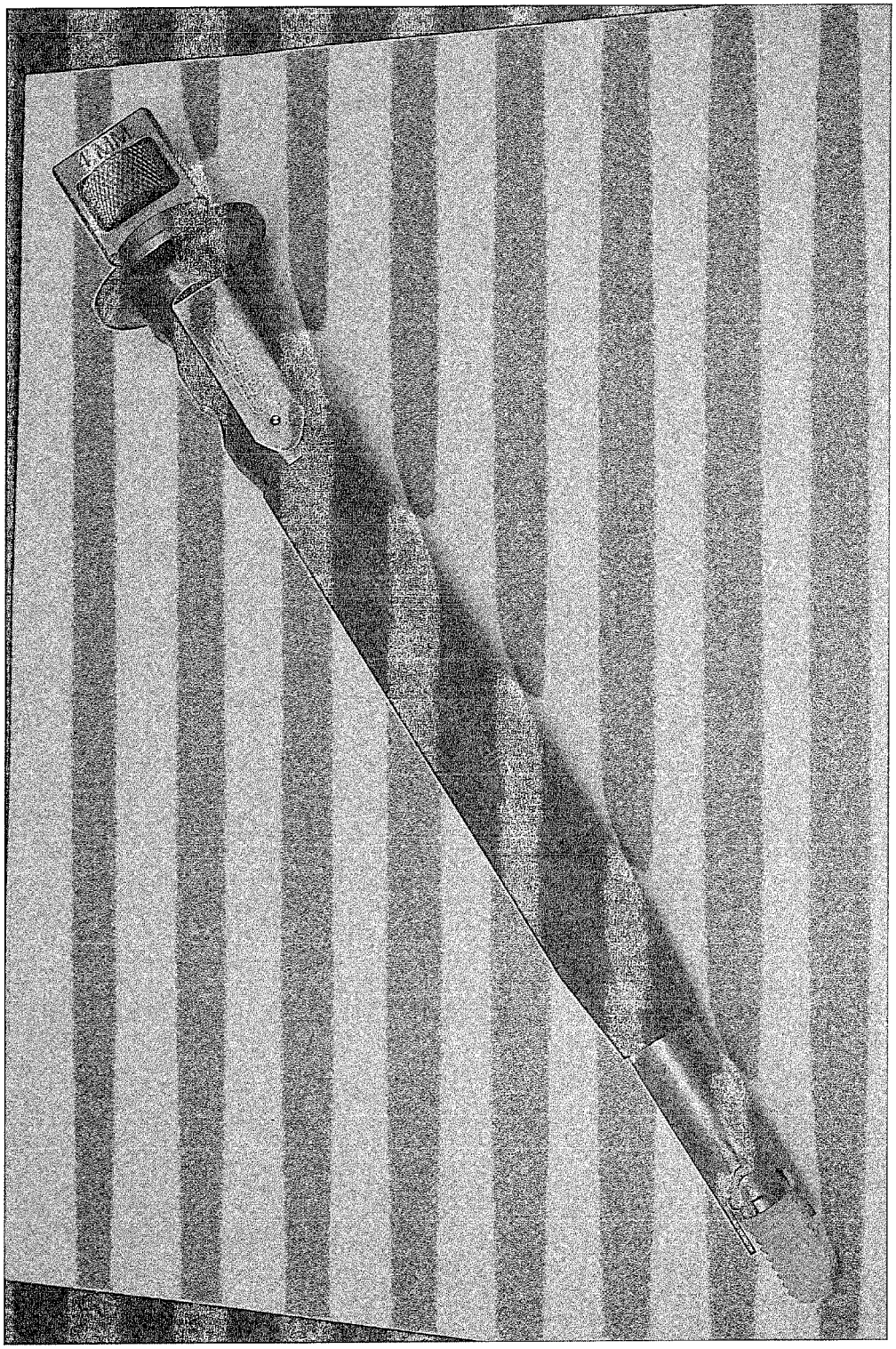
FIG. 27 is a perspective of an implant inserting device engaged with a sacroiliac joint implant.
Figure 28:
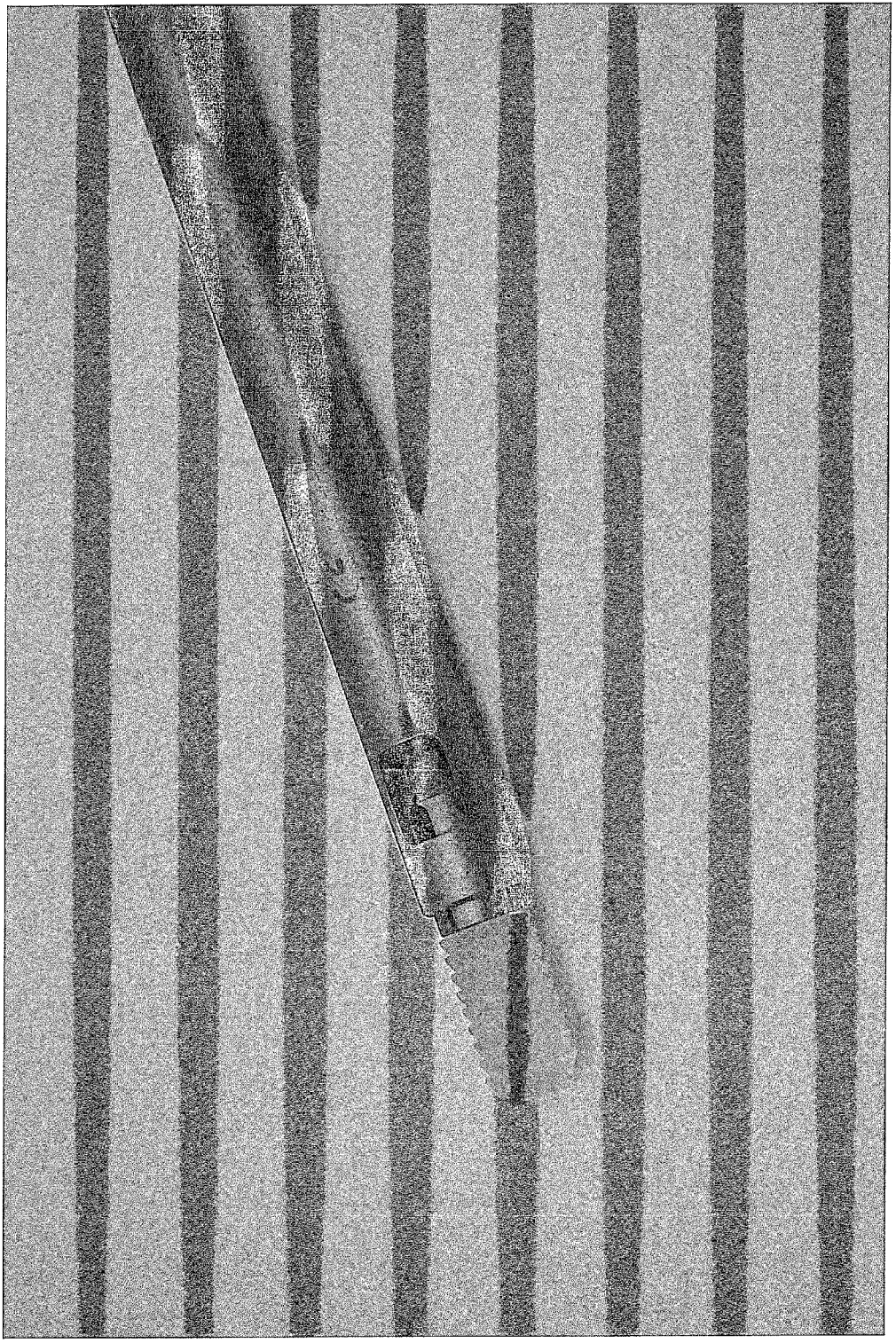
FIG. 28 is a perspective view of a distal end of the implant inserting device of FIG. 27.
Figure 29:
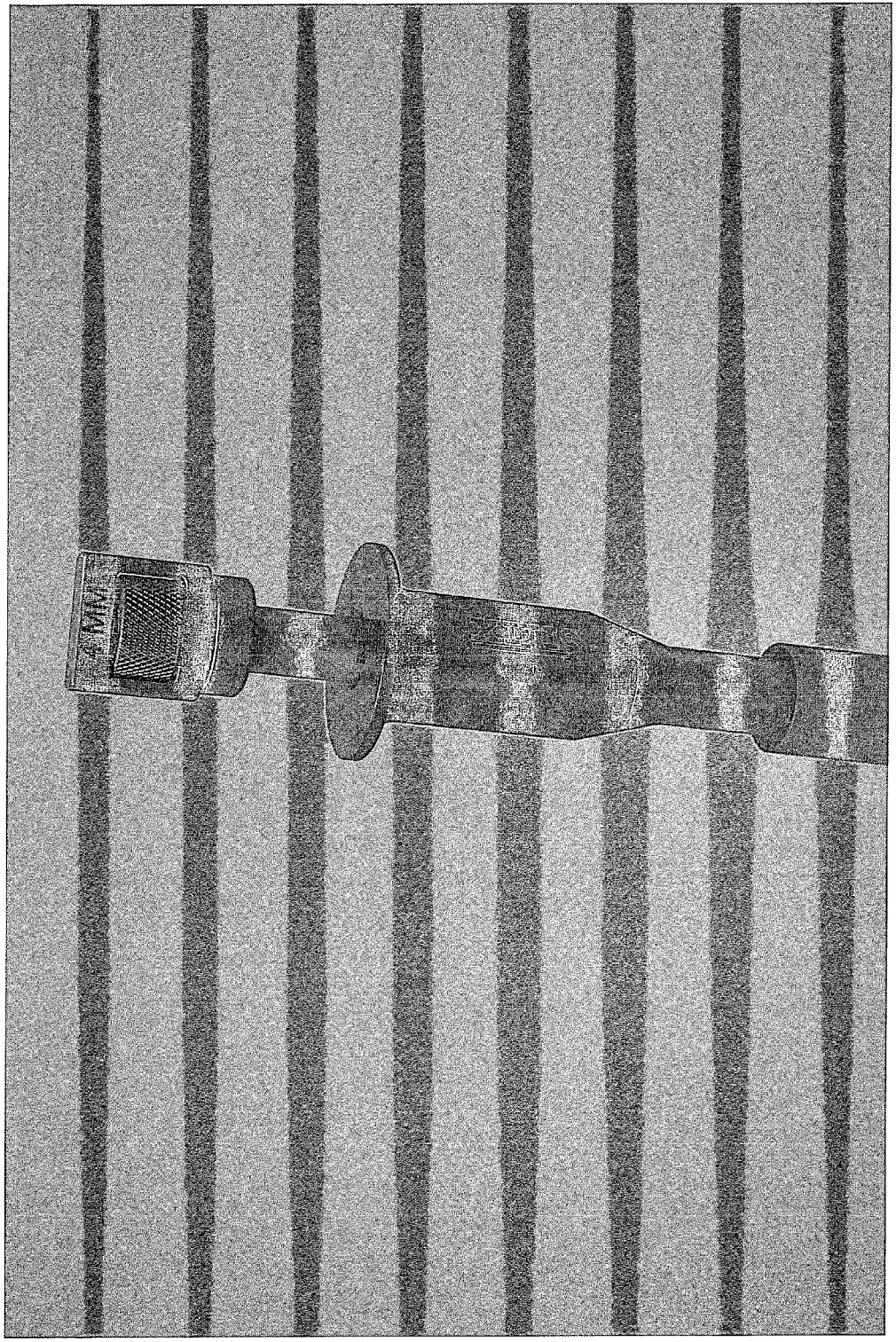
FIG. 29 is a perspective view of a proximal end of the drill guide of FIG. 25 with the implant inserting device partially inserted therein.
Figure 30:
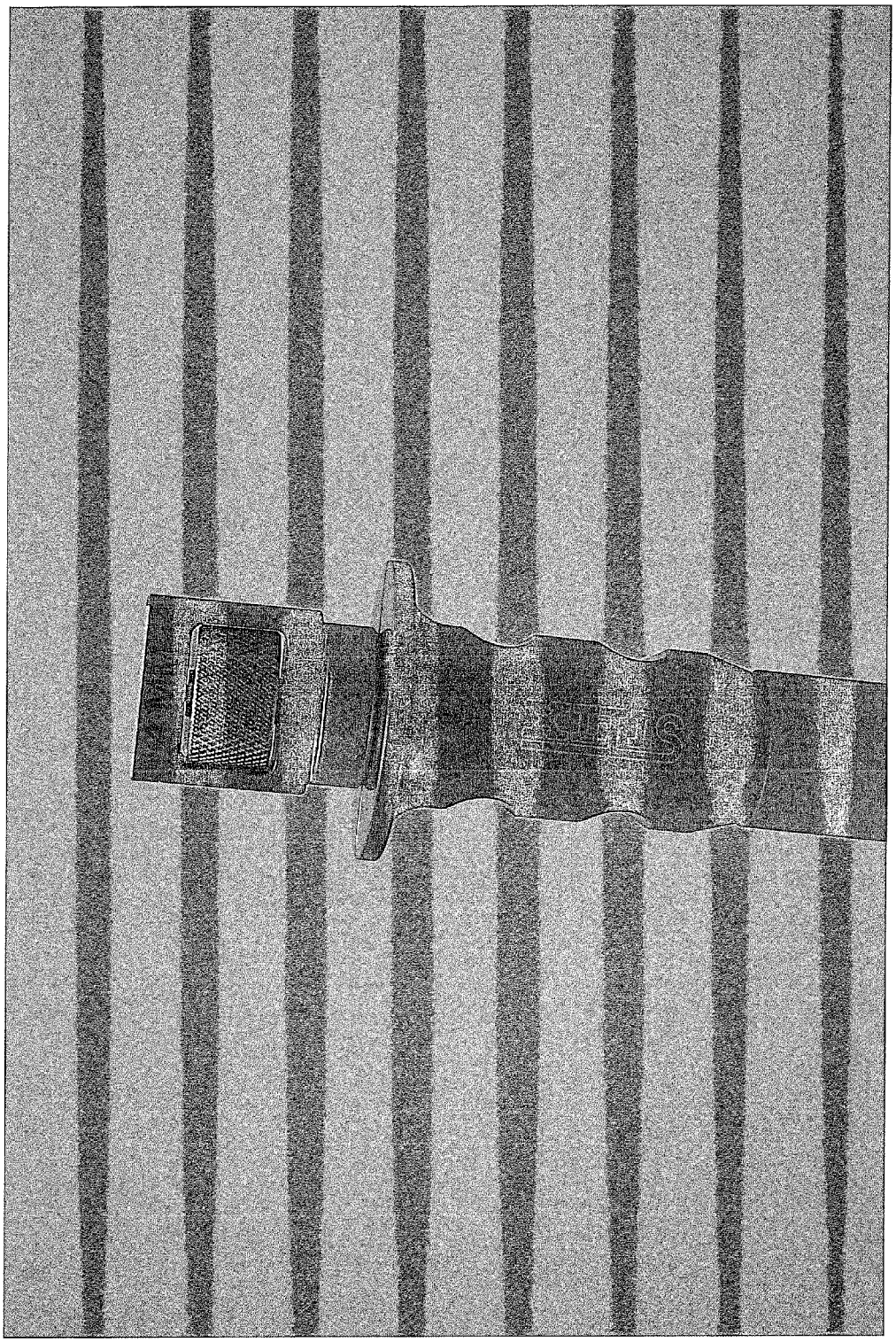
FIG. 30 is a perspective view of the proximal end of the drill guide of FIG. 25 with the implant inserting device fully inserted therein.
Figure 31:
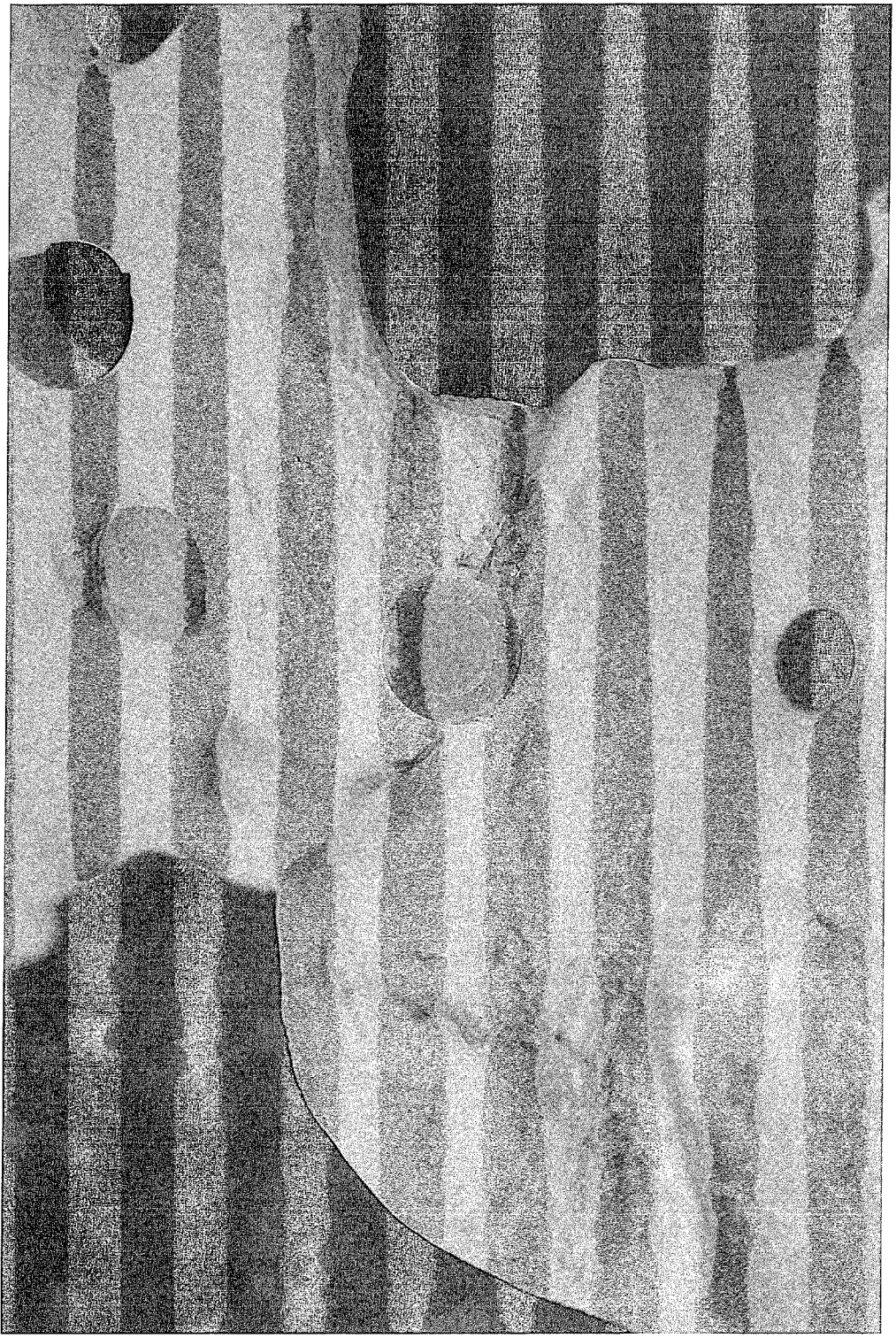
FIG. 31 is a perspective view of the sacroiliac joint implant of FIG. 27 implanted within a sacroiliac joint.

Referring to FIG. 16, joint locator 41 is composed of a hollow tube 43 having a distal end terminating in a pair of spaced, projections 45. Projections 45 are flat, generally planar and separated by an opening extending axially through tube 43. A plurality of ridges are provided on the front and back surfaces of projections 45. The ridges are provided for assisting a physician to locate the projections between the articular surfaces of the sacroiliac joint by tactile sensation.

What follows is a detailed explanation of the procedures used to implant dowels 34 within the sacroiliac joint in accordance with the two configurations shown in FIGS. 1 and 2 utilizing kit 15. FIGS. 16 through 31, which generally illustrate this procedure, are not meant to illustrate the insertion of any particular implant type, such as an inferior implant 28 or superior implant 30, or either the converging or diverging orientations. Rather, the figures are provided to generally describe insertion of the implants using kit 15.

Surgical Zone Identification. Using a direct A-P fluoroscopic view and a radiopaque marker such as a k-wire, the inferior margin of the sacroiliac joint at the level of the posterior inferior iliac spine is identified. This is located at approximately the level of the inferior margin of the S2 foramen and medial and superior to the superior margin of the sciatic notch. A horizontal line (HL1) is drawn through this point marking the inferior edge of the surgical zone. Thereafter, the superior margin of the sacroiliac joint is located, where the anterior and posterior projections of the joint come together. A horizontal line (HL2) is then drawn through the posterior superior iliac spine marking the superior edge of the surgical zone. The most prominent part of the posterior superior iliac spine is located via manual palpation or, if necessary, fluoroscopy, and horizontal line (HL3) is drawn through the posterior superior iliac spine. Lastly, a vertical line (VL1) may be drawn through the posterior superior iliac spine indicating the medial edge of the ilium.

It is important to note that the posterior and anterior edges of the sacroiliac joint should project separately on fluoroscope, with the posterior edge projecting medially and the anterior edge projecting more laterally Preferably, the safe zone identification is made using a straight AP image, confirmed with a lateral view if desired. Angling the x-ray tube cephalad and obliquely assists in visualization of the path of the joint and discrimination of its anterior and posterior edges.

Converging Implants. Inferior implant 28 insertion is initiated by locating a point on the skin approximately 1.5 cm superior to the inferior edge of the surgical zone (HL1) and 1-1.5 cm medial to the medial edge of the ilium (VL1) located and making a small (~2.5 cm) vertical skin incision. If a bilateral sacroiliac joint fusion is planned, depending on individual patient anatomy, it is possible to achieve both fusions through a midline incision at the same level. K-wire 42 is placed through this incision and advanced towards the posterior edge of the sacroiliac joint under fluoroscopic guidance, preferably at a slight (~10 degree) cephalad angle. Once the tip of k-wire 42 contacts bone, the edge of the joint is located and k-wire 42 advanced slightly into the joint, penetrating the ligaments and capsule. While the orientation of the joint varies between individuals, a lateral angle of 10-30% is expected, and approach at the appropriate angle will assist in obtaining access to the joint.

After the position of k-wire 42 is checked via AP and lateral fluoroscopy, k-wire 42 is advanced further. The path of k-wire 42 is checked via fluorosope to ensure that it passes at least 2 cm superior to the superior margin of the sciatic notch. If not, a more cephalad angle is required or k-wire 42 should be removed so that the process can begin from again from a more superior point. K-wire 42 is then advanced to the desired depth, which may later be checked via markings on the k-wire. Alternatively, k-wire 42 can be stopped once the desired trajectory is established. In this event desired implant depth is estimated so as to ensure that there is no penetration anteriorly into the abdominal space. K-wire 42 should not be advanced past the anterior edge of the sacroiliac joint, as visualized via fluoroscopy.

Once the desired k-wire depth is reached, dilators 36 are placed sequentially over k-wire 42, confirming by both feel and fluoroscopy that each one has been advanced as closely as possible into contact with the bony margins of the joint. Once the largest dilator 36 has been placed, the second and third dilators are removed, leaving behind the largest and smallest dilators and k-wire 42. If desired, utilizing a light source and bayoneted instruments the joint can be visually and manually explored to ensure desired placement and the avoidance of significant structures such as large tendons, nerves and vessels. Optionally, Thereafter, drill guide 38 is placed into the joint. The proper alignment of the drill guide may be determined visually prior to placement, or gentle rotation and advancement of drill guide 38 may be used to identify the appropriate alignment by feel. Once the proper alignment has been achieved, drill guide 38 is tamped firmly into the joint.

At this point, the positioning of drill guide 38 and k-wire 42 is checked on A-P and lateral images. If the position of k-wire 42 is used to determine desired depth, it is checked via the markings on the k-wire. If not, an appropriate depth is selected. A sound may be used to determine the position of the drill guide vis-à-vis the joint surface, keeping in mind that the surface of the ilium is often elevated above the surface of the sacrum, which therefore marks the true beginning of the joint. To assist with confirming position of the drill guide or k-wire with the joint, a light source can be clipped to the dilation tube or drill guide and directed downward toward the joint to allow visualization of the joint, k-wire and the teeth of drill guide. Flouroscopy may also be used to check depth and placement. Preferably, the drill depth should be approximately 30 mm below the surface of the joint, allowing for an 8-10 mm countersink of the implant.

Once the positioning of drill guide 38 and k-wire 42 is checked and the desired depth determined, the k-wire and small diameter dilator 36 are removed. Either a manual or power drill bit such as drill 40 is then selected and passed through drill guide 38. Drill 40 is advanced to the desired depth as determined by the markings on the bit. Particularly with manual drill 40, several rotations at the desired depth are needed to ensure that there are no uncut connective tissues entangling the bit. Following cutting, the drill bit is removed. If desired, a small amount of an osteoconductive materials such as DBM or ground cancellous bone may be packed into the bottom of the tunnel formed by the drill prior to placement of the implant.

Once the hole is formed, implant 28 is loaded onto inserter 44, passed through drill guide 38, and tamped firmly into place. Implant 28 is released by turning knob 74 at the proximal end of inserter 44, and the inserter removed. If desired, osteoconductive materials such as DBM or ground cancellous bone may be packed in to fill the remainder of the tunnel formed by the drill. With implant 28 in place, drill guide 38 and remaining dilators 36 are removed.

Optionally, the initial location of the joint for placement of inferior implant 28 can be achieved via arthrogram, using an 18 gauge needle rather than k-wire 42. Once access to the joint has been obtained, proper placement in the joint can be confirmed via injection of contrast dye. A flexible k-wire can then be advanced through the needle into the joint, following the procedures described above from this point.

Superior implant 30 insertion is initiated by identifying a point on the skin approximately 1-1.5 cm superior and 1-1.5 cm medial to the posterior superior iliac spine and making a small (~2.5 cm) vertical incision at that point. K-wire 42 is placed through this incision and advanced towards the sacroiliac joint under fluoroscopic guidance. Depending on individual anatomy, k-wire 42 is inserted at a slight (~10 degree) caudal angle. Due to the alignment of the sacroiliac joint and the overhanging prominence of the ilium, a 25 to 35% lateral angle of approach is expected. Once bony contact is obtained, k-wire 42 is skyved off the anterior edge of the ilium until the entrance to the joint is located. Once entry into the joint has been obtained and confirmed fluoroscopically, the procedure described above for inferior implant 28 can be used for placement of superior implant 30. For placement of superior implants 30, depths greater than 45 mm are not recommended.

Diverging Implants. Diverging implants 28 and 30 insertion is initiated by identifying the posterior superior iliac spine and making a single, small (~2.5 cm) midline incision at the posterior superior iliac spine. Following the steps similar to those described above for insertion of inferior implant 28 of the converging implants, k-wire 42 is placed through this incision at a slightly downward angle below the posterior superior iliac spine and advanced towards the posterior margin of the caudal segment of sacroiliac joint under fluoroscopic guidance. Once the tip of k-wire 42 contacts bone, the edge of the joint is located and k-wire 42 advanced slightly into the joint, penetrating the ligaments and capsule.

After the position of k-wire 42 is checked via AP and lateral fluoroscopy, k-wire 42 is advanced further. The path of k-wire 42 is checked via fluorosope to ensure that it passes at least 2 cm superior to the posterior crest of the caudal segment of the joint. K-wire 42 is then advanced to the desired depth, which may later be checked via markings on the k-wire. Once the desired k-wire depth is reached, dilators 36, joint locator 41 and drill guide 38 are placed sequentially over k-wire 42. Once the proper alignment has been achieved, joint locator 41 is removed, and drill guide 38 is tamped firmly into the joint.

Once the positioning of drill guide 38 and k-wire 42 is checked and the desired depth determined in a similar fashion to that described for converging implants, the k-wire and small diameter dilator 36 are removed. Either a manual or power drill bit such as drill 40 is then selected and passed through drill guide 38. The drill is advanced to the desired depth as determined by the markings on the bit. Following cutting, the drill bit is removed. Once the hole is formed, implant 28 is loaded onto inserter 44, passed through drill guide 38, and tamped firmly into place. Implant 28 is released by turning knob 74 at the proximal end of inserter 44, and the inserter removed. With implant 28 in place, drill guide 38 and remaining dilators 36 are removed.

Superior implant 30 insertion is initiated by adjusting upward and inserting k-wire through the same incision in a slight upward angle. The insertion point is basically right above interior implant 28, offset just enough to avoid drilling out the hole through which implant 28 is implanted. Thus, k-wire 42 is placed through this incision and advanced towards the sacroiliac joint under fluoroscopic guidance. Once entry into the joint has been obtained and confirmed fluoroscopically, the procedure described above for inferior implant 28 can be used for placement of superior implant 30.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed:

1. A method of stabilizing a sacroiliac joint comprising:
   forming a first void and a second void within the articular surfaces of the sacroiliac joint, having a cranial and caudal segment, wherein the first void extends longitudinally along a length of a caudal segment of the articular surfaces of the sacroiliac joint, and
   placing a first implant within the first void and a second implant within the second void,
   wherein the method of stabilizing the sacroiliac joint is performed with essentially no distraction of the sacroiliac joint, wherein the first void extends from a first opening formed in a first posterior periphery section of the caudal segment inferior to a level of a posterior superior iliac spine and the second void extends from a second opening formed in a second posterior periphery section of the caudal segment at or superior to the level of the posterior superior iliac spine.

2. The method according to claim 1 wherein the first void extends anterocranially within the caudal segment of the articular surfaces of the sacroiliac joint and the second void extends anterocaudally within the articular surfaces of the sacroiliac joint.

3. The method according to claim 2 wherein the second void extends within a midsection portion of the articular surfaces of the sacroiliac joint that is formed between the caudal segment and a cranial segment of the articular surfaces of the sacroiliac joint.

4. The method according to claim 1 wherein the first implant, the second implant or both the first implant and the second implant are a cancellous bone implant including a tapered distal end portion and a midsection including a plurality of acutely pointed, continuous ridges configured for preventing the cancellous bone implant from backing out of the sacroiliac joint.

5. The method according to claim 1 wherein forming the first void within the articular surfaces of the sacroiliac joint includes inserting a wire into the sacroiliac joint, inserting a dilation tube over the wire thereby dilating tissue and creating a posterior access to the sacroiliac joint, providing a drill guide having a distal end with a pair of opposing teeth, inserting the drill guide into the dilation tube and sliding the drill guide along the dilation tube, inserting the teeth into a space between an ilium bone and a sacrum bone thereby stabilizing the drill guide, inserting a drill bit through the drill guide and into the sacroiliac joint, rotating the drill bit and removing a portion of articulating surfaces of the ilium bone and the sacrum bone.

6. The method according to claim 1 further comprising delivering a fusion promoting substance through a tube into the first void and partially filling the first void with the fusion promoting substance.

7. The method according to claim 1 further comprising delivering the first implant through a tube into the first void using an implant inserter device.

8. The method according to claim 1 wherein the implant inserter device includes a grasping member holding the first implant and a rotatable member coupled to the grasping member, the grasping member releasing the first implant into the first void upon rotation of the rotatable member.

9. The method according to claim 1 further comprising counter-sinking the first implant into the first void.

10. The method according to claim 9 further comprising delivering a fusion promoting substance through a tube into an unfilled portion of the first void.

11. The method according to claim 1 wherein the first implant and the second implant are maintained within the articular surfaces of the articular joint by a friction fit.

12. The method according to claim 1 wherein the sacroiliac joint is not distracted.

13. The method according to claim 1 wherein the sacroiliac joint is distracted less than 1.0 mm.

14. A method of stabilizing a sacroiliac joint comprising:
    forming a first void and a second void within articular surfaces of the sacroiliac joint, having a cranial and caudal segment, and
    placing a first implant within the first void and a second implant within the second void,
    wherein the first void extends anterocranially and longitudinally along a length of a caudal segment of the articular surfaces of the sacroiliac joint and the second void extends anterocaudally within the articular surfaces of the sacroiliac joint, and wherein the first void extends from a first opening formed through a first posterior margin of a posterior crest of the caudal segment.

15. The method according to claim 14 wherein the first opening is inferior to a level of a posterior superior iliac spine and the second void extends from a second opening formed in a second posterior margin section of the sacroiliac joint at or superior to the level of the posterior superior iliac spine.

16. The method according to claim 14 wherein the second void extends within a midsection portion of the articular surfaces of the sacroiliac joint, the midsection portion being formed by and between the caudal segment and a cranial segment of the articular surfaces of the sacroiliac joint.

17. The method according to claim 16 wherein the method of stabilizing the sacroiliac joint is performed with essentially no distraction of the sacroiliac joint.

18. The method according to claim 14 wherein the first implant, the second implant or both the first implant and the second implant are a bone implant including a tapered distal end portion, a substantially flat proximal end face having a central protuberance extending axially therefrom and a midsection extending between the distal end portion and the proximal end face, the midsection including a plurality of ridges configured for preventing the bone implant from backing out of the sacroiliac joint.

19. The method according to claim 14 wherein forming the first void, the second void or both the first void and the second void within the articular surfaces of the sacroiliac joint includes using one or more dilation tubes to dilate tissue and create a posterior access to the sacroiliac joint, sliding a drill guide terminating in teeth along a first dilation tube of the one or more dilation tubes, inserting the teeth into a space between an ilium bone and a sacrum bone, inserting a drill bit through the drill guide and removing a portion of articulating surfaces of the ilium bone and the sacrum bone.

20. The method according to claim 14 further comprising placing a fusion promoting substance into the first void, the second void or both first void and the second void and partially filling the first void, the second void or both the first void and the second void with the fusion promoting substance.

21. The method according to claim 14 further comprising counter-sinking the first implant into the first void.

22. The method according to claim 21 further comprising placing a fusion promoting substance into an unfilled portion of the first void.

23. The method according to claim 14 further comprising providing a kit containing a bone dowel implant having a plurality of ridges, one or more dilation tubes, a drill guide, a drill bit, and a bone dowel inserter.

24. The method according to claim 14 wherein the first implant has a first longitudinal axis and the second implant has a second longitudinal axis, the first longitudinal axis and the second longitudinal axis crossing at an angle ranging between 50 degrees and 40 degrees.

25. A method of stabilizing a sacroiliac joint comprising:
    forming a first passageway extending anterocranially within the articular surfaces, having a cranial and caudal segment: of a the sacroiliac joint from a first opening formed in a first posterior margin section of a posterior crest of the sacroiliac joint,
    forming a second passageway extending anterocaudually within the articular surfaces of the sacroiliac joint from a second opening formed in a second posterior margin section of the sacroiliac joint, and
    placing a first implant within the first passageway and a second implant within the second passageway, wherein the first passageway extends along a longitudinal axis of the caudal segment of the articular surfaces of the sacroiliac joint.

26. The method according to claim 25 wherein the method of stabilizing the sacroiliac joint is performed with essentially no distraction of the sacroiliac joint.

27. The method according to claim 25 wherein the first implant is compressed between the articular surfaces of the sacroiliac joint.

28. The method according to claim 25 wherein the second passageway extends within a midsection portion of the articular surfaces of the sacroiliac joint, the midsection portion being formed by and between a caudal segment and a cranial segment of the articular surfaces of the sacroiliac joint.

29. The method according to claim 25 further comprising,
    forming a third passageway extending anterocranially within the articular surfaces of the sacroiliac joint from a third opening formed in a third posterior margin section of the sacroiliac joint that laterally opposes the first posterior margin section,
    forming a fourth passageway extending anterocaudually within the articular surfaces of the sacroiliac joint from a fourth opening formed in a fourth posterior margin section of the sacroiliac joint that laterally opposes the second posterior margin section, and
    placing a third implant within the third passageway and a fourth implant within the fourth passageway.

\* \* \* \* \*